United States Patent [19]

Chan et al.

[11] 4,231,944

[45] Nov. 4, 1980

[54] FLUORINATED POLYENES

[75] Inventors: Ka-Kong Chan, Hopatcong; Beverly A. Pawson, Verona, both of N.J.

[73] Assignee: Hoffmann-La Roche Inc., Nutley, N.J.

[21] Appl. No.: 37,803

[22] Filed: May 10, 1979

Related U.S. Application Data

[60] Division of Ser. No. 936,466, Aug. 24, 1978, Pat. No. 4,171,318, which is a continuation of Ser. No. 809,738, Jun. 24, 1977, Pat. No. 4,137,246, which is a continuation-in-part of Ser. No. 722,939, Sep. 13, 1976, abandoned, which is a continuation-in-part of Ser. No. 632,028, Nov. 14, 1975, abandoned.

[51] Int. Cl.$^3$ .............. C07D 307/16; C07D 307/12; C07D 333/24
[52] U.S. Cl. .............. 260/347.4; 260/347.3; 260/347.8; 549/76; 549/78; 549/79; 424/275; 424/285
[58] Field of Search .............. 260/347.3, 347.4, 347.8, 260/332.2 R, 332.2 A, 332.3 R; 549/76, 78, 79

[56] References Cited

U.S. PATENT DOCUMENTS

| | | | |
|---|---|---|---|
| 3,883,508 | 5/1975 | Cook | 260/211.5 R |
| 3,984,440 | 10/1976 | Bollag et al. | 260/345.2 |
| 4,054,589 | 10/1977 | Bollag et al. | 260/408 |
| 4,061,656 | 12/1977 | Klaus | 260/332.2 A |
| 4,086,420 | 5/1978 | Tsuchihashi | 542/413 |

FOREIGN PATENT DOCUMENTS

2651979  5/1977  Fed. Rep. of Germany.

OTHER PUBLICATIONS

Englert Helv. Chim. Acta, 58:2367–2376 (1975).
Wilkoff et al., Cancer Research, 36:964 (1976).

*Primary Examiner*—John F. Niebling
*Attorney, Agent, or Firm*—Jon S. Saxe; Bernard S. Leon; George W. Johnston

[57] ABSTRACT

9-substituted, 4- or 6-fluorine substituted retinoic acid derivatives useful as antitumor agents and in the treatment of acne as well as a method for their manufacture are disclosed. Substituents at the 9-position include substituted phenyl, thienyl and furyl groups.

5 Claims, No Drawings

FLUORINATED POLYENES

RELATED APPLICATIONS

This patent application is a division of U.S. patent application Ser. No. 936,466, filed Aug. 24, 1978, now U.S. Pat. No. 4,171,318, which in turn is a continuation of U.S. patent application Ser. No. 809,738, filed June 24, 1977 now U.S. Pat. No. 4,137,246 which in turn is a continuation-in-part of U.S. patent application Ser. No. 722,939, filed Sept. 13, 1976, now abandoned, which in turn is a continuation-in-part of U.S. patent application Ser. No. 632,028, filed Nov. 14, 1975, now abandoned.

SUMMARY

The present invention concerns compounds having the formula:

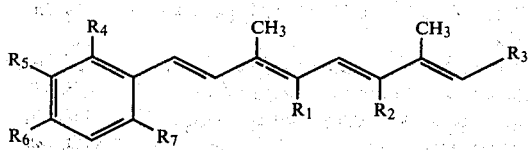

wherein one of $R_1$ and $R_2$ is fluorine and the other is hydrogen; $R_3$ is formyl, hydroxymethyl, alkoxymethyl, carboxyl, alkoxycarbonyl, carbamoyl, mono(lower alkyl)-carbamoyl or di(lower alkyl)-carbamoyl; at least one of $R_4$, $R_5$ and $R_7$ is halogen and the others are hydrogen or lower alkyl; and $R_6$ is lower alkyl or lower alkoxy; or pharmaceutically acceptable salts thereof.

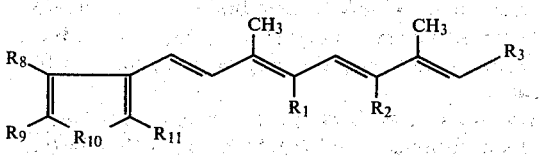

wherein one of $R_1$ and $R_2$ is fluorine and the other is hydrogen; $R_3$ is formyl, hydroxymethyl, alkoxymethyl, carboxyl, alkoxycarbonyl, carbamoyl, mono(lower alkyl)-carbamoyl or di(lower alkyl)-carbamoyl; $R_8$ and $R_{11}$ each are lower alkyl; $R_9$ is hydrogen or lower alkyl; and $R_{10}$ is oxygen or sulphur; with the proviso that when $R_3$ is alkoxycarbonyl and $R_{10}$ is sulphur, the compound is all trans; or pharmaceutically acceptable salts thereof.

The compounds of formulas I and II are useful as antitumor agents as well as for the treatment of acne, psoriasis and other related dermatological disorders.

DETAILED DESCRIPTION OF THE INVENTION

The present invention concerns fluorinated polyene compounds, a process for the manufacture thereof and pharmaceutical preparations containing same.

The polyene compounds included within the present invention have the formula:

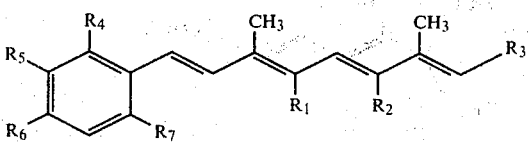

wherein one of $R_1$ and $R_2$ is fluorine and the other is hydrogen; $R_3$ is formyl, hydroxymethyl, alkoxymethyl, carboxyl, alkoxycarbonyl, carbamoyl, mono(lower alkyl)-carbamoyl or di(lower alkyl)-carbamoyl; at least one of $R_4$, $R_5$ and $R_7$ is halogen and the others are hydrogen or lower alkyl; and $R_6$ is lower alkyl or lower alkoxy; or pharmaceutically acceptable salts thereof.

As used herein lower alkyl means alkyl groups having from 1 to 7 carbon atoms, (e.g., methyl, ethyl, n-propyl and isopropyl). Lower alkoxy means alkoxy groups having from 1 to 7 carbon atoms (e.g., methoxy, ethoxy and isopropoxy). Alkoxymethyl and alkoxycarbonyl include straight chain or branched-chain alkoxy groups having from 1 to 20 carbon atoms (e.g., methoxy, ethoxy, isopropoxy and cetyloxy). Lower alkoxy groups contain from 1 to 7 carbon atoms and are preferred. Aryl denotes mononuclear aromatic hydrocarbon groups such as phenyl, tolyl and the like which can be unsubstituted or substituted in one or more positions with halogen, nitrogen, lower alkyl or lower alkoxy and polynuclear aryl groups such as napthyl, anthryl, phenanthryl, azulyl and the like which can be unsubstituted or substituted with one or more of the aforementioned substituents.

The alkanoyloxy groups present in the alkanoyloxymethyl group are derived from alkanecarboxylic acids having from 1 to 20 carbon atoms (e.g., acetic acid, propionic acid, pivalic acid, palmitic acid and stearic acid). The preferred group of alkanecarboxylic acids are lower alkanecarboxylic acids having from 1 to 7 carbon atoms. The carbamoyl groups within the scope of this invention can be monosubstituted or disubstituted by straight chain or branched chain lower alkyl groups. Examples of such substituted carbamoyl groups are methyl carbamoyl, dimethylcarbamoyl and diethylcarbamoyl. Halogen includes all four halogens, fluorine, chlorine, bromine and iodine. Alkali metals include lithium, sodium, potassium and rubidium. Alkaline earth metals include beryllium, magnesium, calcium and strontium. Pharmaceutically acceptable salts means any conventional pharmaceutically acceptable salt. Among the preferred salts are alkali metal, alkaline earth metal (e.g., sodium, potassium and calcium) and substituted or unsubstituted ammonium salts.

Unless otherwise indicated, all formulas include cis-/trans mixtures as well as the corresponding cis and trans compounds.

All trans compounds of formula I are preferred.

Compounds of formula I wherein $R_3$ is alkoxycarbonyl, carboxy or carbamoyl are also preferred. According to another embodiment of the compounds of formula I, at least one of $R_4$, $R_5$ and $R_7$ is halogen and the others are lower alkyl.

Additionally, polyene compounds having the following formula are contemplated by the present invention:

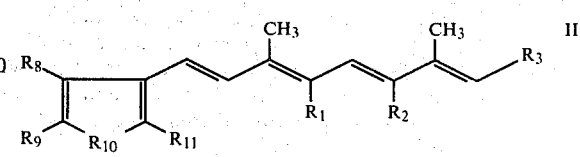

wherein one of $R_1$ and $R_2$ is fluorine and the other is hydrogen; $R_3$ is formyl, hydroxymethyl, alkoxymethyl, carboxyl, alkoxycarbonyl, carbamoyl, mono(lower alkyl)-carbamoyl or di(lower alkyl)-carbamoyl; $R_8$ and $R_{11}$ each are lower alkyl; $R_9$ is hydrogen or lower alkyl; and $R_{10}$ is oxygen or sulphur; with the proviso that when $R_3$ is alkoxycarbonyl and $R_{10}$ is sulphur, the compound is all trans; or pharmaceutically acceptable salts thereof.

All trans compounds of formula II are preferred.

Compounds of formula II wherein $R_3$ is alkoxycarbonyl, carboxy or carbamoyl also are preferred.

The compounds of formula I or formula II are pharmacodynamically valuable. They are effective in regressing the growth of tumors such as papillomas.

The compounds of formulas I and II are also useful as medicaments for the topical and systemic therapy of acne, psoriasis and other related dermatological disorders which are characterized by an increased or pathologically altered cornification, as well as inflammatory and allergic dermatological conditions. They can also be used to treat disorders which are characterized by inflammatory or degenerative alterations of the mucous membranes. Advantageously, the inventive compounds are only slightly toxic.

To examine their pharmacodynamic properties, the compounds of the present invention were subjected to skin papilloma tests as described by W. Bollag in *Experentia*, Vol. 27 (1971) pp. 90 et seq. and to hypervitaminosis-A dosage experiments as explained by W. Bollag in *Europ. J. Cancer*, Vol. 10 (1974) pp. 731–737. The following Table illustrates the results of the inventive compounds in these tests.

TABLE I

| Compound of Example | hypervitaminosis dose mg/kg/day | Papilloma Effect Dose mg/kg/week | Effect ± % regression |
| --- | --- | --- | --- |
| 3 | 50 | 100 | −59 |
|   |    | 50  | −60 |
|   |    | 25  | −41 |
| 4 | 50 | 100 | −59 |
|   |    | 50  | −42 |
|   |    | 25  | −36 |
| 18 | 200 | 200 | −41 |
| 19 | 100 | 100 | −47 |
| 20 | 200 | 400 | −64 |

The compounds of formulas I and II can be used as medicaments in the form of pharmaceutical preparations which contain at least one of these compounds in association with a compatible carrier material.

Pharmaceutical preparations for systemic administration illustratively can be prepared by adding a polyene compound of formula I or II as the active ingredient to pharmaceutically acceptable, non-toxic, inert, solid or liquid carriers which are usually included in such preparations. The pharmaceutical preparations can be administered enterally, parenterally or topically. Suitable preparations for enteral administration are, for example, tablets, capsules, dragees, syrups, suspension, solutions and suppositories. Suitable pharmaceutical preparations for parenteral administration are infusion solutions.

The dosages in which the compounds are administered can be varied according to the mode and route of administration and according to the requirements of the patient. For example, the compounds can be administered in amounts of from 5 mg. to 100 mg. daily in one or more dosages.

In addition to the active compounds of this invention, the pharmaceutical preparations can contain pharmaceutically acceptable inert or pharmacodynamically active additives. For example, tablets or granules can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor improving additives and pharmaceutically acceptable substances commonly used as preservatives, stabilizers, moisture retainers or emulsifiers, salts for varying the osmotic pressure, buffers and other pharmaceutically acceptable additives can also be present in the pharmaceutical preparations.

The aforementioned pharmaceutically acceptable carrier materials and diluents are well known to the pharmaceutical compounding art and can be organic or inorganic substances such as water, gelatin, lactose, magnesium stearate, talc, gum arabic, polyalkyleneglycols and the like. It is, of course, a prerequisite that all adjuvants used in the preparation of the pharmaceutical preparations are non-toxic and pharmaceutically acceptable.

For topical administration, the compounds of this invention are expediently prepared as salves, tinctures, creams, solutions, lotions, sprays, suspensions and the like. Ointments, creams and solutions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

Conventional pharmaceutically acceptable antioxidants (e.g., tocopherol, N-methyl-α-tocopheramine butylated hydroxyanisole and butylated hydroxytoluene) can also be incorporated into the pharmaceutical preparations containing the polyene compounds of this invention.

In accordance with the present invention, the compounds of formulas I and II wherein $R_2$ is fluorine and $R_3$ is alkoxycarbonyl may be formed by the process described hereinbelow.

A compound of the formula:

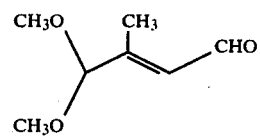

III can be reacted via a conventional Horner reaction with a compound of the formula:

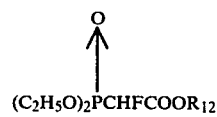

IV to form a compound of the formula:

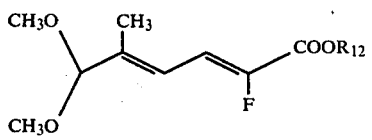

V wherein $R_{12}$ is lower alkyl.

In this reaction temperature is not critical and can range from about −78° to about 60° C., preferably −10° to 35° C.

Compound V is hydrolyzed by basic hydrolysis to form a compound of the formula:

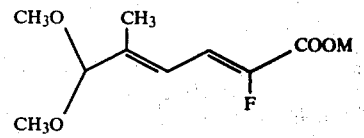

VI wherein M is an alkali metal.

Any conventional means of hydrolyzing an ester to an alkali metal salt may be utilized. Among the applicable methods is treating compound V with an alkali metal hydroxide such as lithium hydroxide. Temperature is not critical and can range from about 0° to about 100° C., preferably 20° to 50° C.

Compound VI is then converted by treatment with a methyl organo metallic reagent (e.g., methyl lithium) to a compound of the formula:

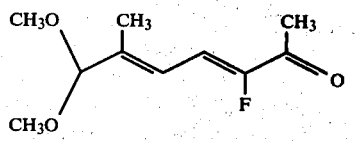

VII by conventional means. Although not critical, temperature can range from about −78° to about 50° C., preferably −78° to 0° C.

Compound VII can be reacted via a Horner reaction with a compound of the formula:

VIII and the resulting acetal can be subjected to acid hydrolysis to yield a compound of the formula:

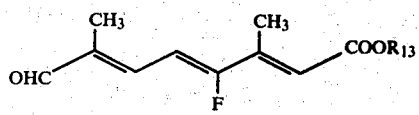

IX wherein $R_{13}$ is lower alkyl.

Temperature is not critical and can range from about 0° to about 60° C., preferably 10 to 35° C.

Compound IX may be reacted with a phosphonium salt of the formula:

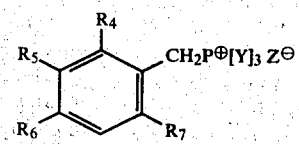

X via a Wittig reaction to form the inventive compounds of formula I wherein $R_2$ is fluorine and $R_3$ is alkoxycarbonyl, which have the formula:

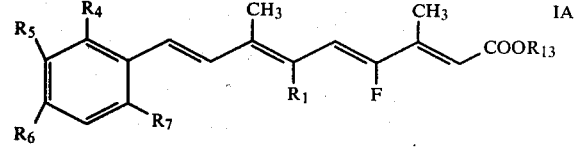

IA wherein $R_1$ is hydrogen, $R_4$–$R_7$ and $R_{13}$ are as above; Y is aryl and Z is the anion of an organic or inorganic acid.

According to the present invention, compound IX also can react with a phosphonium salt of the formula:

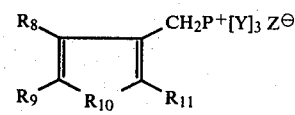

XI via a Wittig reaction to form the inventive compounds of formula II wherein $R_2$ is fluorine and $R_3$ is alkoxycarbonyl, which have the formula:

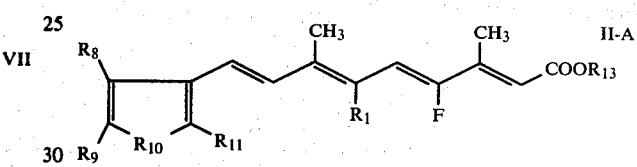

II-A wherein $R_1$ is hydrogen, $R_8$–$R_{11}$, $R_{13}$, Y and Z are as above.

According to the above Wittig procedure, compounds IX and X or XI are repectively reacted in the presence of any inorganic or organic acid-binding agent. Typical acid binding agents include alkali metal hydroxide and alcoholates (e.g., sodium hydroxide and sodium methylate), tertiary amines (e.g., triethylamine and pyridine) and alkylene oxides which may be alkyl-substituted (e.g., ethylene oxide and 1,2-butylene oxide). Although not necessary, the reaction may proceed in any invert solvent such as a chlorinated hydrocarbon (e.g., methylene chloride and dimethylformamide). The temperature and pressure of the reaction is not critical but generally the reaction occurs between room temperature and the boiling point of the reaction mixture and at atmospheric pressure. Room temperatures is preferred.

In formulas X and XI, aryl denoted by X includes all aryl groups and preferably mononuclear aryl groups such as phenyl, lower alkyl-phenyl and lower alkoxyphenyl (e.g., tolyl, xylyl, mesityl and p-methoxyphenyl). The inorganic acid anions denoted by Z include, for example, chloride, bromide, iodide and hydrosulphate ions. A preferred organic acid anion for Z is the tosyloxy ion.

In a preferred embodiment, compound X has the formula:

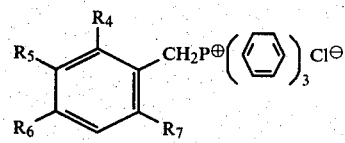

X-A wherein $R_4$–$R_7$ are as above.

In a preferred embodiment, compound XI has the formula:

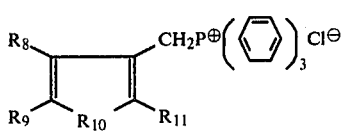

wherein $R_8$–$R_{11}$ are as above.

The compounds of formula X and XI can be formed by any convention method for producing a substituted phosphonium salt. For example, a substituted benzene having the formula:

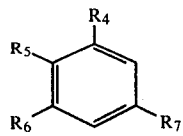

or substituted thiophene or substituted furan having the formulas:

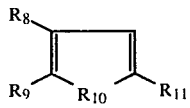

is treated with formaldehyde in the presence of a hydrohalic acid (e.g., concentrated hydrochloric acid) to form a halide of the formula:

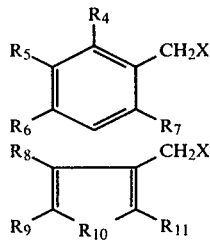

wherein X is halogen and $R_4$–$R_{11}$ are as above.

The reaction optionally occurs in a solvent such as glacial acetic acid. Temperature and pressure are not critical and can range from about 0° to about 150° C. The preferred temperature values are from about 20° to about 100° C. The resulting halide of formula XIV or XV is then reacted via a Wittig reaction with a triarylphosphine to yield compounds of formula X or XI respectively. Typical triarylphosphines include triphenylphosphine and tritolylphosphine. Although not necessary, the Wittig reaction preferably occurs in a solvent such as any organic aromatic hydrocarbon (e.g., benzene, toluene). In the Wittig reaction, temperature is not critical and can range from about −50° to about 100° C. The preferred temperature values are from about 10° to about 80° C.

If desired, the above compounds of formula X or XI wherein Z is an inorganic acid can be transformed to compounds of formula X or XI wherein Z is an organic anion by any conventional means to exchange a halide for an organic anion. For example, compounds of formula X or XI wherein Z is haloacid can be treated with silver tosylate to yield a silver halide and the compound for formula X or XI wherein Z is an organic anion.

In accordance with the present invention, compounds of formulas I and II wherein $R_1$ is fluorine and $R_3$ is alkoxycarbonyl can be formed by the process described hereinbelow.

A compound of the formula:

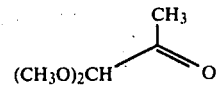

is reacted via a Horner reaction with compound IV to form a mixture of a Z stereoisomer of the formula:

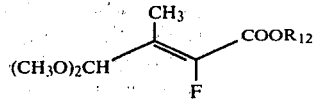

and an E stereoisomer of the formula:

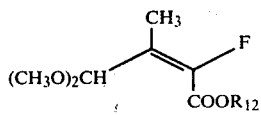

wherein $R_{12}$ is lower alkyl.

The Z and E stereoisomers then are separated by any conventional means such as by distillation.

The Z stereoisomer (compound XVII-Z) can be reduced to a compound of the formula:

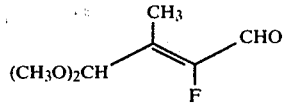

Any conventional means for reducing an ester to an aldehyde can be employed. For example, compound XVII-Z can be treated with a dialkyl aluminum hydride such as diisobutyl aluminum hydride in the cold to form compound XVIII. Temperature is not critical and can range from about −78° to about 50° C. The preferred temperature values are from about −78° to about −0° C.

Additionally, the E stereoisomer (compound XVII-E) can be converted to compound XVIII via intermediate:

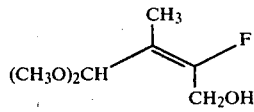

Compound XVII-E is transformed to compound XIX by any conventional method for forming an alcohol from an ester. For example, compound XVII can be treated with diisobutyl aluminum hydride to form compound XIX. Temperature is not critical and can range from about −78° to about 50° C., preferably −78° to 0° C.

Oxidation of compound XIX affords compound XVIII. Any conventional method of oxidizing an alcohol to an aldehyde can be employed. Illustratively, compound XIX can be treated with manganese dioxide in a suitable solvent to yield compound XVIII. Temperature is not critical and can range from about −10° to about 100° C. The preferred temperature values are from about 0° to about 35° C.

Compound XVIII is then reacted via a Horner reaction with a compound of the formula:

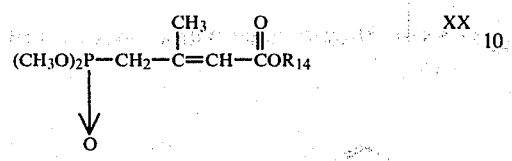

or via a Wittig reaction with

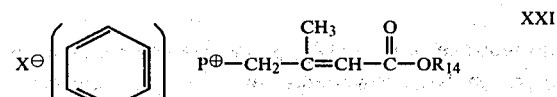

to form a compound of the formula:

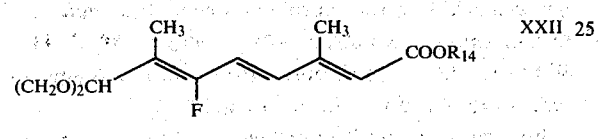

wherein X is halogen and $R_{14}$ is lower alkyl.

In the Horner or Wittig reaction, temperature is not critical. For the Horner reaction, the preferred temperature range is from about −78° to about 100° C. The Wittig reaction is preferably carried out at a temperature range of about −78° to about 200° C.

Compound XXII is then converted to a compound of the formula:

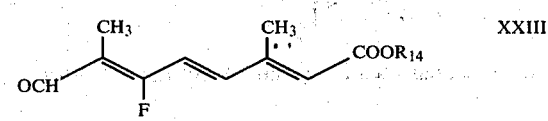

wherein $R_{14}$ is as above.

Any conventional method of converting an acetal to an aldehyde can be employed. Acid hydrolysis is a suitable method. For example, compound XXII can be treated with hydrochloric acid and diethyl ether to form compound XXIII. Temperature is not critical and can range from about 0° to about 60° C. The preferred temperature values are from about 10° to about 35° C.

Compound XXIII can be reacted with compound X via a Wittig reaction to form compounds of formula I wherein $R_1$ is fluorine and $R_3$ is alkoxycarbonyl, which have the formula:

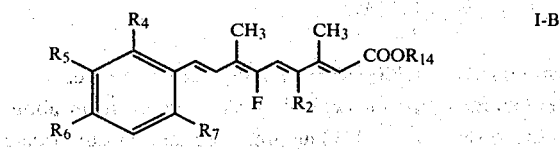

wherein $R_2$ is hydrogen, $R_4$–$R_7$ and $R_{14}$ are as above.

Alternatively, compound XXIII can be reacted with compound XI via a Wittig reaction to form compounds of formula II wherein $R_1$ is fluorine and $R_3$ is alkoxycarbonyl which have the formula:

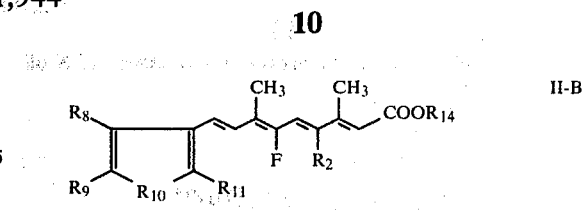

wherein $R_2$ is hydrogen, $R_8$–$R_{11}$ and $R_{14}$ are as above.

The Wittig procedure for reacting compound XXIII with compound X or XI is the same as the Wittig reaction described above with respect to the reaction of compound IX with compound X or XI.

In accordance with another aspect of the present invention, compounds of formula I wherein $R_3$ is alkoxycarbonyl can also be formed by the process described hereinbelow.

Compound XVI of the formula:

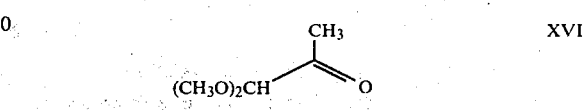

is reacted via a Horner reaction with compound VIII of the formula:

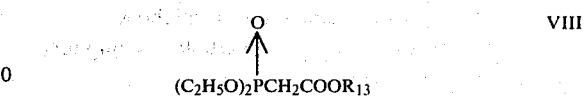

or with compound IV of the formula:

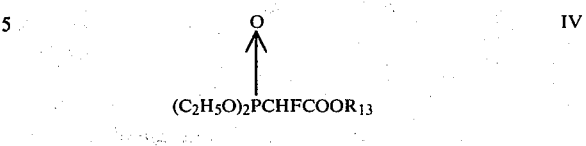

to form a compound of the formula:

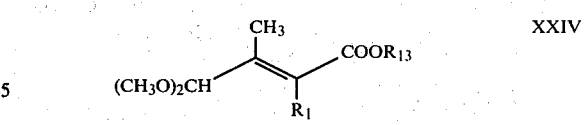

wherein $R_1$ and $R_{13}$ are as above.

Temperature is not critical and can range from about −78° to about 60° C. The preferred temperature values are from about −10° to about 35° C.

Compound XXIV then can be converted to a compound of the formula:

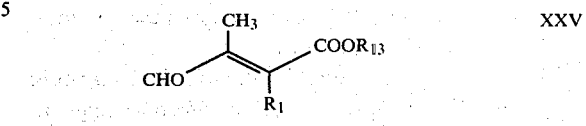

wherein $R_1$ and $R_{13}$ are as above.

Any conventional means for transforming an acetal to an aldehyde can be employed. A suitable method includes acid hydrolysis under conventional conditions of compound XXIV to compound XXV. Temperature is not critical and can range from about 0° to about 60° C. The preferred temperature values are from about 10° to about 35° C.

Compound XXV can be reacted with compound X of the formula:

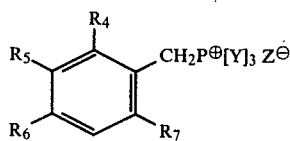 X via a Wittig reaction to form a mixture of Z and E stereoisomers of the formula:

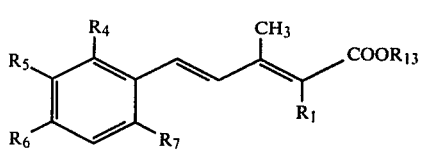 XXVI wherein $R_1$, $R_4$–$R_7$, $R_{13}$, Y and Z are as above.
Temperature is not critical and can range from about −50° to about 100° C. The preferred temperature values are from about 10° to about 80° C.

The Z and E stereoisomers of formula XXVI then can be separated by any conventional method.

Compound XXVI can be converted to compound XXVII of the formula:

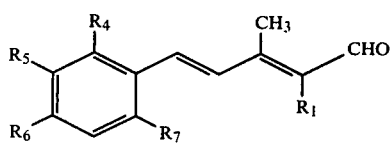 XXVII wherein $R_1$, $R_4$–$R_7$ are as above, via intermediate:

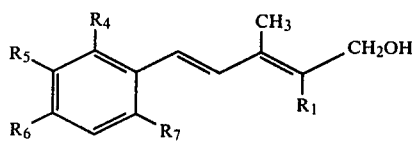 XXVIII wherein $R_1$, $R_4$–$R_7$ are as above.
Compound XXVI is transformed to compound XXVIII by any conventional method of forming an alcohol from an ester. For example, compound XXVI can be treated with diisobutyl aluminum hydride to form compounds XXVIII. Temperature is not critical and can range from about −78° to about 50° C. The preferred temperature is from about −78° to about 0° C.

Oxidation of compound XXVIII affords compound XXVII. Any conventional method for oxidizing an alcohol to an aldehyde can be employed. Illustratively, compound XXVIII can be treated with manganese dioxide in a suitable solvent to yield compound XXVII. Temperature is not critical and can range from about −10° to about 100° C. The preferred temperature values are from about 0° to about 35° C.

Compound XXVII can be reacted via a Horner reaction with a compound of the formula:

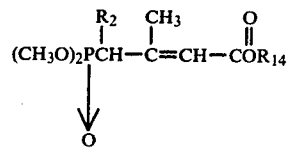 XXIX or via a Wittig reaction with a compound of the formula:

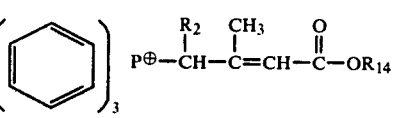 XXX wherein one of $R_1$ and $R_2$ is fluorine and the other is hydrogen, $R_{14}$ is lower alkyl and X is a halide; to form compounds of formula I wherein $R_3$ is alkoxycarbonyl.

In the Horner or Wittig reaction, the temperature is not critical. For the Horner reaction, the preferred temperature is from about −78° to about 100° C. The Wittig reaction is preferably carried out at a temperature range of about −78° to about 200° C.

In accordance with a further aspect of the present invention, compounds of formula II wherein $R_3$ is alkoxycarbonyl can also be formed in a manner similar to the aforementioned process. More particularly, compound XXV of the formula:

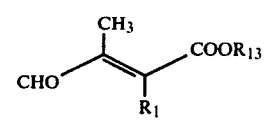 XXV can be reacted with compound XI of the formula:

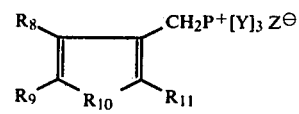 XI via a Wittig reaction to form a mixture of E and Z stereoisomers of the formula:

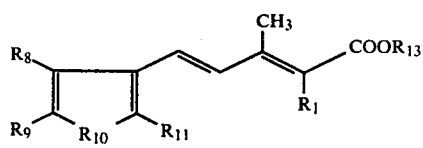 XXXI wherein $R_1$, $R_8$–$R_{11}$, $R_{13}$, Y and Z are as above.
Temperature is not critical and can range from about −78° to about 200° C. The preferred temperature range is from about 0° to about 100° C.

The Z and E stereoisomers of formula XXXI then are separated by any conventional means.

Compound XXXI can be converted to compound XXXII of the formula:

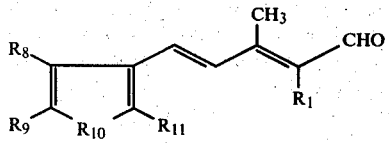

wherein $R_1$, $R_8$–$R_{11}$ are as above, via intermediate:

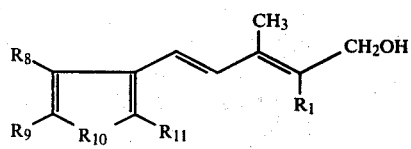

wherein $R_1$, $R_8$–$R_{11}$ are as above.

Compound XXXI is transformed to compound XXXIII by any conventional method of forming an alcohol from an ester. For example, compound XXXI can be treated with diisobutyl aluminum hydride to form compounds XXXIII. Temperature is not critical and can range from about −78° to about 50° C. The preferred temperature values are from about −78° to about 0° C.

Oxidation of compound XXXIII affords compound XXXII. Any conventional method for oxidizing an alcohol to an aldehyde can be employed. Illustratively, compound XXXIII can be treated with manganese dioxide in a suitable solvent to yield compound XXXII. Temperature is not critical and can range from about −10° to about 100° C. The preferred temperature values are from about 0° to about 35° C.

Compound XXXII can be reacted via a Horner reaction with compound XXIX of the formula:

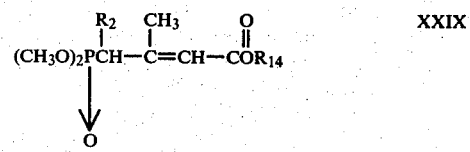

or via a Wittig reaction with compound XXX of the formula:

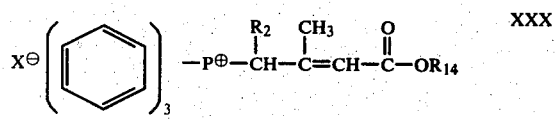

wherein one of $R_1$ and $R_2$ is fluorine and the other is hydrogen, $R_{14}$ is lower alkyl and X is halide to form compounds of formula II wherein $R_3$ is alkoxycarbonyl.

In the Horner or Wittig reaction, temperature is not critical. For the Horner reaction, the preferred temperature range is are from about −78° to about 100° C. The Wittig reaction is preferably carried out at a temperature range of about −78° to about 200° C.

According to the present invention, additional procedures may be applied to any of the above processes to produce compounds of formulas I and II wherein $R_3$ is formyl, hydroxymethyl, alkoxymethyl, carboxyl, carbamoyl, mono(lower alkyl)-carbamoyl or di(lower alkyl)carbamoyl. Typical processes contemplated by the present invention include: hydrolyzing or amidating a carboxylic acid ester obtained according to the above process steps; esterifying or amidating a carboxylic acid obtained according to the above; reducing a carboxylic acid or carboxylic acid ester obtained according to the above process steps to the corresponding alcohol and optionally etherifying or esterifying said alcohol; saponifying an alcohol ester or hydrolysis of an acetal obtained according to the above process steps; or oxidizing an alcohol or alcohol ester obtained according to the above.

More particularly, a carboxylic acid ester of formula I or II (i.e., wherein $R_3$ is alkoxycarbonyl) can be hydrolyzed to a corresponding carboxylic acid (wherein $R_3$ is carboxyl) in any conventional manner. For example, the carboxylic acid ester may be treated with alkali, especially aqueous-alcoholic sodium hydroxide or potassium hydroxide at a temperature between room temperature and the boiling point of the mixture to form a carboxylic acid. The resulting acid can then be amidated to form the compound of formula I or II wherein $R_3$ is carbamoyl via an acid halide. Alternatively, a carboxylic acid ester can be directly amidated to form the compound of formula I or II wherein $R_3$ is carbamoyl by treatment with lithium amide. This treatment is advantageously carried out at room temperature.

A carboxylic acid of formula I or II (i.e., wherein $R_3$ is carboxyl) can be converted into an acid halide in any conventional manner. For example, the carboxylic acid may be treated with thionyl chloride, preferably in pyridine, to form an acid halide. The acid halide then can be converted into an ester (i.e., the compound of formula I or II wherein $R_3$ is alkoxycarbonyl) by reaction with an alkanol. Alternatively, the acid halide can be converted to a compound of formula I or II where $R_3$ is carbamoyl by reaction with ammonia where it is desired to convert the acid halide to the corresponding compound of formula I or II wherein $R_3$ is carbamoyl. Where $R_3$ is mono(lower alkyl)-carbamoyl, the acid halide is reacted with a mono(lower alkyl)-amine such as mono-methylamine, mono-ethylamine, etc. On the other hand, where it is desired to convert the acid halide to the corresponding compound of formula I or II where $R_3$ is a di(lower alkyl)-carbamoyl, the halide is reacted with a di(lower alkyl)-amine such as dimethylamine, di-ethylamine, ethylmethylamine, etc. Any conventional method of reacting an acid halide with an amine or with ammonium can be utilized to produce the compounds of formula I or II where $R_3$ is mono(lower alkyl)-carbamoyl or di(lower alkyl)-carbamoyl.

A carboxylic acid (i.e., wherein $R_3$ is carboxyl) or a carboxylic acid ester (i.e., wherein $R_3$ is alkoxycarbonyl) of formula I or II can be reduced to a corresponding alcohol represented by formula I or II wherein $R_3$ is hydroxymethyl in any conventional manner. The reduction is advantageously carried out using a metal hydride or an alkyl metal hydride in an inert solvent. Examples of hydrides especially suitable for the reduction are mixed metal hydrides such as lithium aluminum hydride or bis-(2-methoxy-ethoxy)-sodium aluminum hydride. Suitable inert solvents are, inter alia, ether, tetrahydrofuran or dioxane when lithium aluminum hydride is used, and ether, hexane, benzene or toluene when diisobutylaluminum hydride or bis-(2-methoxyethoxy)sodium aluminum hydride is used.

An alcohol represented by formula I or II (i.e., wherein $R_3$ is hydroxymethyl) can be etherified with an alkyl halide, (e.g., ethyl iodide), for example, in the presence of a base (preferably sodium hydride), in an organic solvent such as dioxane, tetrahydrofuran, 1,2-dimethoxyethane or dimethylformamide at a temperature between 0° C. and room temperature. An alcohol represented by formula I or II can be esterified by treatment with an alkanoyl halide or anhydride, conveniently in the presence of a base (e.g., pyridine or triethylamine) at a temperature between room temperature and the boiling point of the mixture.

An alcohol ester as obtained above can be saponified in a conventional manner. For example, the saponification in the manner previously described in connection with the hydrolysis of a carboxylic acid ester is a suitable manner.

An alcohol represented by formula I or II (i.e., wherein $R_3$ is hydroxymethyl) or an ester thereof (wherein $R_3$ is alkoxycarbonyl) can be oxidized in a conventional manner to give a corresponding carboxylic acid represented by formula I or II wherein $R_3$ is carboxyl. The oxidation is advantageously carried out using silver (I) oxide and an alkali in water or in a water-miscible organic solvent at a temperature between room temperature and the boiling point of the oxidation mixture.

An alcohol represented by formula I (i.e., wherein $R_3$ is hydroxymethyl) can be oxidized to the compound of formula I wherein $R_3$ is formyl by treatment with any oxidizing agent capable of converting an alcohol to an aldehyde. Magnesium dioxide is a suitable oxidizing agent.

The compounds of formulas I and II can occur as a cis/trans mixture which can be separated in a known manner into the corresponding cis and trans components or isomerized in a known manner to the all-trans compounds. Any conventional method of double bond isomerization may be utilized to form the all-trans compounds. For example, a cis/trans mixture of either compound I or compound II can be treated with catalytic amounts of iodine in an organic solvent (e.g., benzene and toluene) to produce the desired all-trans product. Temperature is not critical and can range from about 10° to about 60° C. The preferred temperature values are from about 25° to about 35° C.

The following Examples illustrate the present invention. The ether is diethyl ether and temperatures are expressed in degrees Celsius (° C.) unless otherwise specified. In the Examples, "work up in the usual manner" connotes that the following procedure was performed: The reaction mixture was partitioned between water and an organic solvent (e.g., diethyl ether, methylene chloride). The organic extracts were combined, washed with water or brine, dried with magnesium sulfate or sodium sulfate, filtered and evaporated under reduced pressure on a rotary evaporator.

EXAMPLE 1

Ethyl (E/Z,E)-2-fluoro-6,6-dimethoxy-5-methyl-2,4-hexadienoate

A suspension of 100.84 g. (2.10 mol) of sodium hydride (50% oil dispersion; the oil had been removed by washing with pentane) in 200 ml. of dry dimethoxyethane was stirred at 4° C. under argon white a solution of 5.08.62 g. (2.10 mol) of triethyl phosphonofluoroacetate in 500 ml. of dry dimethoxyethane was added dropwise. The resulting mixture was stirred at 23° C. for 1.5 hours. To the resulting orange-brown mixture, a solution of 300 g. (2.08 mol) of 4,4-dimethoxy-3-methyl-2-butenal in 500 ml. of dry dimethoxyethane was added dropwise over a period of 1.0 hour with ice-bath cooling and stirring under argon. The reaction mixture was stirred at 23° C. for 17 hours and further at 60° C. for 3 hours under argon. The mixture was cooled to about 20° C. and 500 ml. of cold water was slowly added thereto. The resulting solution was further diluted with 1.5 l. of water and worked up with ether in the usual manner to give 486.2 g. of crude product. Vacuum distillation of this material yielded 281 g. (58% yield) of ethyl (E/Z,E)-2-fluoro-6,6-dimethoxy-5-methyl-2,4-hexadienoate as a colorless liquid, bp. 99°–117° C./0.6–0.75 mm. Hg.

EXAMPLE 2

Ethyl (E,Z,E)-4-fluoro-3,7-dimethyl-8-oxo-2,4,6-octatrienoate

A solution of 100 g. (0.43 mol) of ethyl (E/Z,E)-2-fluoro-6,6-dimethoxy-5-methyl-2,4-hexadienoate in 1.0 l. of absolute ethanol was stirred with 10.82 g. (0.45 mol) of lithium hydroxide at 23° C. under argon for 20 hours. The residual lithium hydroxide was removed by filtration and washed with 200 ml. of absolute ethanol. Evaporation of ethanol to dryness at reduced pressure gave 105.3 g. of yellow oil. This material was further dried at 23° C. over phosphorous pentoxide at 0.5 mm. for 24 hours which yielded 92.4 g. of (E/Z,E)-2-fluoro-6,6-dimethoxy-5-methyl-2,4-hexadienoic acid lithium salt as a yellow semisolid. A sample of 74.76 g. (0.379 mol) of this lithium salt was dissolved in 600 ml. of dry tetrahydrofuran and cooled to −72° C. in a dry ice-acetone bath. A solution of 188.5 ml. (0.379 mol) of methyl lithium (2.01 M in ether) was added dropwise to the above solution, with stirring at −72° C. under argon. After 15 minutes of stirring, another 37.7 ml. (0.076 mol) of methyl lithium was slowly added thereto. The resulting reaction misture was stirred at −72° C. under argon for 1.0 hour and then was allowed to come to 23° C. Water (250 ml.) was slowly added to the reaction mixture and most of the tetrahydrofuran was removed at reduced pressure. The resulting solution was worked up with ether in the usual manner to give 56.86 g. (74% yield) of (E/Z,E)-3-fluoro-7,7-dimethoxy-6-methyl-3,5-heptadien-2-one as a yellow liquid.

While stirring at 23° C. under argon, a solution fo 75.55 g. (0.337 mol) of triethyl phosphonoacetate in 200 ml. of dry dimethoxyethane was added dropwise to a suspension of 16.17 g. (0.337 mol) of a 50% sodium hydride oil dispersion (the oil was removed by washing with pentane) in 25 ml. of dimethoxyethane. The resulting mixture was then stirred at 23° C. under argon for 1.0 hour and a solution of 55.71 g. (0.275 mol) of (E/Z,E)-3-fluoro-7,7-dimethoxy-6-methyl-3,5-heptadien-2-one in 200 ml. of dry dimethoxyethane was added dropwise thereto. The reaction mixture was stirred at 23° C. for 2.0 hours and then diluted with ice-water and adjusted to pH 2 with approximately 350 ml. of 1 N hydrochloric acid. The resulting solution was worked up with ether in the usual manner to give 52.46 g. of crude product. This material was filtered through 500 g. of florisil with 1:1 ether-petroleum ether to yield 42.91 g. of ethyl (E,E/Z,E)-4-fluoro-3,7-dimethyl-8-oxo-2,4,6-octatrienoate. This compound was dissolved in 1.5 l. of anhydrous ether and treated with 493 mg. of iodine crystals. The resulting solution was stirred at 23° C. under argon for 24 hours, washed with a 5% sodium thiosulfate solution and dried over anhydrous magnesium sulfate. The ether solution was concentrated to a small volume at reduced pressure and then passed onto 600 g. of florisil. Elution with ether afforded 40.65 g. of yellow-orange crystals, which on recrystallization from ether-petroleum ether yielded 26.47 g. (41% yield from ketone) of ethyl (E,Z,E)-4-fluoro-3,7-dimethyl-8-oxo-2,4,6-octatrienoate as orange crystals, mp. 70°–74° C.

EXAMPLE 3

Ethyl (E,Z,E,E)-9-(6-chloro-4-methoxy-2,3-dimethylphenyl)-4-fluoro-3,7-dimethyl-2,4,6,8-nonatetraenoate A mixture of 6.0 g. (12.46 mmol) of 6-chloro-4-methoxy-2,3-dimethylbenzyl triphenylphosphonium chloride and 2.71 g. of ethyl (E,Z,E)-4-fluoro-3,7-dimethyl-8-oxo-2,4,6-octatrienoate in 15 ml. of 1,2-butylene oxide was heated at 110° C. in a sealed tube for 60 hours. The resulting mixture was worked up with ether in the usual manner to give 13.53 g. of crude product. This material was chromatographed on 300 g. of silica gel. Elution with 1:4 ether-petroleum ether yielded 4.65 g. of yellow crystals. Recrystallization of this material from methylene chloride-petroleum ether afforded 1.67 g. (35% yield) of pure ethyl (E,Z,E,E)-9-(6-chloro-4-methoxy-2,3-dimethylphenyl)-4-fluoro-3,7-dimethyl-2,4,6,8-nonatetraenoate as yellow crystals, mp. 126°–128° C.

EXAMPLE 4

Ethyl (E,Z,E,E)-4-fluoro-3,7-dimethyl-9-(2,4,5-trimethyl-3-thienyl)-2,4,6,8-nonatetraenoate A mixture of 10.0 g. (22.8 mmol) of (2,4,5-trimethyl-3-thenyl) triphenylphosphonium chloride and 5.09 g. (22.5 mmol) of ethyl (E,Z,E)-4-fluoro-3,7-dimethyl-8-oxo-2,4,6-octatrienoate in 50 ml. of 1,2-butylene oxide was heated in a sealed tube at 110° C. for 48 hours. Work-up in the usual manner gave 21.97 g. of brown oily substance. This brown material was chromatographed on 700 g. of silica gel. Elution with ether-petroleum ether (1:9 parts by volume) yielded 3.69 g. of oily product. On crystallization from hexane the oily product afforded 1.97 g. of ethyl (E,Z,E,E)-4-fluoro-3,7-dimethyl-9-(2,4,5-trimethyl-3-thienyl)-2,4,6,8-nonatetraenoate as yellow crystals, mp. 73°–75° C.

EXAMPLE 5

Ethyl (E,Z,E,E)-9-(3-chloro-2,4,6-trimethylphenyl)-4-fluoro-3,7-dimethyl-2,4,6,8-nonatetraenoate A mixture of 6.0 g. (12.89 mmol) of 5-chloro-2,4,6-trimethylbenzyl triphenylphosphonium chloride and 2.82 g. (12.5 mmol) of ethyl (E,Z,E)-4-fluoro-3,7-dimethyl-8-oxo-2,4,6-octatrienoate in 30 ml. of 1,2-butylene oxide was heated in a sealed tube at 110° C. for 48 hours. Workup in the usual manner gave 10.95 g. of brown oil which was chromatographed on 500 g. of silica gel. Elution with ether-petroleum ether (1:9 parts by volume) gave 2.24 g. of crude product which on crystallization from hexane yielded 1.76 g. of ethyl (E,Z,E,E)-9-(3-chloro-2,4,6-trimethylphenyl)-4-fluoro-3,7-dimethyl-2,4,6,8-nonatetraenoate as yellow crystals, mp. 100°–104° C.

EXAMPLE 6

Ethyl (E,Z,E,E)-9-(2-chloro-4-methoxy-3,6-dimethylphenyl)-4-fluoro-3,7-dimethyl-2,4,6,8-nonatetraenoate A mixture of 4.45 g. (10 mmol) of 2-chloro-4-methoxy-3,6-dimethylbenzyl triphenylphosphonium chloride and 2.0 g. of (8.83 mmol) of ethyl (E,Z,E)-4-fluoro-3,7-dimethyl-8-oxo-2,4,6-octatrienoate in 200 ml. of toluene and 150 ml. of 1,2-butylene oxide was heated at 85°–90° C. and stirred for 16 hours under argon. The resulting solution was worked up in the usual manner and purified by column chromatography on 150 g. of silica gel with dichloromethane as eluant to yield 4.41 g. of crystalline product. This material was recrystallized from dichloromethane-petroleum ether (1:30 parts by volume) to give 1.80 g. of ethyl (E,Z,E,E)-9-(2-chloro-4-methoxy-3,6-dimethylphenyl)-4-fluoro-3,7-dimethyl-2,4,6,8-nonatetraenoate as yellow crystals, mp. 115°–117° C.

EXAMPLE 7

Ethyl (E,Z,E,E)-9-(2,3,6-trichloro-4-methoxyphenyl)-4-fluoro-3,7-dimethyl-2,4,6,8-nonatetraenoate A mixture of 2.36 g. (9.54 mmol) of 2,3,6-trichloro-4-methoxybenzyl triphenylphosphonium chloride and 2.0 g. (8.93 mmol) of ethyl (E,Z,E)-4-fluoro-3,7-dimethyl-8-oxo-2,4,6-octatrienoate in 200 ml. of toluene and 150 ml. of 1,2-butylene oxide was heated at 85°–90° C. under argon for 18 hours. The mixture was worked up in the usual manner and the resulting crude product was filtered through 150 g. of silica gel. Elution with methylene chloride gave 2.48 g. of a yellow crystalline substance. Recrystallization of this material from methylene chloride-isopropyl ether yielded 2.21 g. (58% yield) of ethyl (E,Z,E,E)-9-(2,3,6-trichloro-4-methoxyphenyl)-4-fluoro-3,7-dimethyl-2,4,6,8-nonatetraenoate as yellow crystals, mp. 140°–142.5° C.

EXAMPLE 8

Ethyl (E,Z,E,E)-9-(2,6-dichloro-4-methoxy-3-methylphenyl)-4-fluoro-3,7-dimethyl-2,4,6,8-nonatetraenoate A solution of 4.3 ml. (9.8 mmol) of n-butyllithium (2.3 M in hexane) was added under argon, at −72° C., to a stirred suspension of 3.86 g. (7.7 mmol) of 2,6-dichloro-4-methoxy-3-methylbenzyl triphenylphosphonium chloride in 30 ml. of dry tetrahydrofuran. The resulting mixture was stirred at −30° C. until an orange solution formed. The orange solution was further cooled to −72° C. and a solution of 1.6 g. (7.1 mmol) of ethyl (E,Z,E)-4-fluoro-3,7-dimethyl-8-oxo-2,4,6-octatrienoate in 10 ml. of dry tetrahydrofuran was slowly added thereto. The temperature of the reaction mixture was gradually raised to 23° C. and the mixture was stirred at this temperature under argon for 2.0 hours. The resulting mixture was worked up in the usual manner to give 6.75 g. of crude product which was chromatographed on 150 g. of silica gel. Elution with etherpetroleum ether (1:9 parts by volume) gave 1.59 g. of yellow crystalline substance which on recrystallization from methylene chloride-hexane afforded 1.09 g. of ethyl (E,Z,E,E)-9-(2,6-dichloro-4-methoxy-3-methylphenyl)-4-fluoro-3,7-dimethyl-2,4,6,8-nonatetraenoate as yellow crystals, mp. 127°–132° C.

EXAMPLE 9

Ethyl (E)-and (Z)-2-fluoro-4,4-dimethoxy-3-methyl-2-butenoate

Sodium hydride (64 g. 1.33 mol, 50% dispersion in mineral oil) was suspended in 1500 ml. of dimethylformamide (dried over calcium oxide and distilled at reduced pressure) in a 3 l. round-bottomed flask fitted with a thermometer, mechanical stirrer, argon inlet and dropping funnel. The resulting mixture was cooled to 0° C. and triethylphosphonofluoroacetate (312 g. 1.29 mol) was added slowly thereto over a 30 minute period. Stirring was continued for an additional 30 minutes and then 1.95 g. of glyoxal dimethylacetal (1.65 mol) were added slowly thereto. The resulting mixture was stirred for 1 hour, poured into 3 l. of water and extracted with 1.5 l. of hexane. The hexane extract was washed twice with 0.5 l. of water and with 0.5 l. of a saturated sodium chloride solution. The combined organic extract was dried with sodium sulfate, filtered and distilled to remove most of the hexane. The product, which was sensitive to strong base, acid, and moisture, was distilled at 65°-68° C. (3 mm.) to give 184 g. (68%) of about a 35:65 ratio of ethyl (E) and (Z)-2-fluoro-4,4-dimethoxy-3-methyl-2-butenoate.

EXAMPLE 10

Z-2-fluoro-3-methyl-4,4-dimethoxy-2-buten-1-al 15.8 g. (77 mmol) of ethyl Z-2-fluoro-4,4-dimethoxy-3-methyl-2-butenoate was dissolved in 250 ml. of hexane in a 500 ml. round-bottomed flask fitted with a thermometer, argon inlet and dropping funnel. The resulting mixture was cooled to −75° C. and 63.5 ml. of di-isobutylaluminum hydride (1.45 equivalent of hydrogen) were added slowly thereto. The reaction mixture was stirred for 1 hour. Ethyl acetate (8.8 g., 100 mmol) was added thereto and the reaction mixture was allowed to come to −30° C. A mixture of 20 g. of sodium sulfate containing 3.6 g. of water was added thereto and stirring continued for 1 hour at 25°-35° C. The resulting material was twice filtered through celite and evaporated on a rotary evaporator at 31° C. (in glassware which had been rinsed with 8 N ammonium hydroxide and dried) to yield Z-2-fluoro-3-methyl-4,4-dimethoxy-2-buten-1-al obtained (approximately 10 g.). An inert gas atmosphere was maintained during all workup operations.

EXAMPLE 11

Methyl 2(E,Z),4(E),6(Z)-8,8-dimethoxy-3,7-dimethyl-6-fluoro-2,4,6-octatrienoate

Dimethyl-(2-methyl-3-carbomethoxy-2-propen-1-yl) phosphonate (18.0 g., 81 mmol) was dissolved in 250 ml. of anhydrous tetrahydrofuran in a 500 ml. round-bottomed flask fitted with a thermometer, argon inlet and septum. The solution was cooled to −60° C. and 36.0 ml. of n-butyllithium (2.3 M, 83 mmol) was added slowly thereto via a syringe. The mixture was stirred for 0.5 hours at −60° C. and Z-2-fluoro-3-methyl-4,4-dimethoxy-2-buten-1-al (prepared from 15.8 g. of ethyl Z-2-fluoro-4,4-dimethoxy-3-methyl-2-butenoate) was added at −60° C. The reaction mixture was allowed to warm to 0°-5° C. for 0.5 hours, was poured into 2 l. of water and extracted with 1.5 l. of hexane. The hexane extract was washed twice with 0.5 l. of water and then with 0.5 l. of a saturated sodium chloride solution, dried with 100 g. of sodium sulfate, filtered and evaporated to give 12.5 g. (63% yield) of methyl 2(E,Z),4(E),6(Z)-8,8-dimethoxy-3,7-dimethyl-6-fluoro-2,4,6-octatrienoate.

EXAMPLE 12

Methyl 2(E),4(E),6(Z)-3-methyl-6-fluoro-7-formyl-2,4,6-octatrienoate

Methyl 2(E,Z),4(E),6(Z)-3,7-dimethyl-6-fluoro-8,8-dimethoxy-octa-2,4-trienoate (12.5 g. 48 mmol) was dissolved in 250 ml. of hexane in an argon atmosphere and 250 ml. of 3 N hydrochloric acid were added with vigorous stirring. After 0.5 hours, 200 ml. of diethyl ether was added thereto to dissolve the solid material. The organic phase was separated and the aqueous layer was extracted with 100 ml. of hexane. The organic extracts were combined and washed with 200 ml. of water and 200 ml. of a saturated sodium chloride solution, dried with 50 g. of sodium sulfate, filtered and evaporated.

Crystallization at −20° C. from 500 ml. of ether-hexane (1:1 parts by volume) gave 3.95 g. (38%) of 2(E),-4(E),6(Z)-3-methyl-6-fluoro-7-formyl-2,4,6-octatrienoate. The mother liquor was recrystallized from 600 ml. of ether-hexane (1:1.2 parts by volume) at −70° C. to yield 5.95 g. (58%) of 2(E,Z)4(E),6(Z)-3-methyl-6-fluoro-7-formyl-2,4,6-octatrienoate. This product was isomerized to give the desired 2(E),4(E),6(Z)-isomer.

EXAMPLE 13

E-4,4-dimethoxy-2-fluoro-3-methyl-2-buten-1-ol

E-2-fluoro-4,4-dimethoxy-3-methyl-2-butenoate (60 g., 0.29 mol) was dissolved in 2500 ml. of pentane (in a 5000 ml. round-bottomed flask fitted with an argon inlet, thermometer, dropping funnel and magnetic stirrer) and cooled to −70° C. Diisobutylaluminum hydride (496 ml., 870 mmol, 3.0 eq.) was added slowly over a 1 hour period and stirring continued for 2 hours. 44 g. (0.5 mol) of ethyl acetate were added thereto and the temperature was allowed to rise to 30° C.

Sodium sulfate (200 g.) containing 54 g. of water was added to the reaction mixture and the temperature was maintained at 30° C. for 2 hours. The resulting material was filtered twice through Celite under argon and evaporated on a rotary evaporator at 31° C. (in a flask which had been rinsed with 8 N ammonium hydroxide and dried) to yield E-4,4-dimethoxy-2-fluoro-3-methyl2-buten-1-ol. An inert gas atmosphere was maintained during all work-up operations.

EXAMPLE 14

E-4,4-dimethoxy-2-fluoro-3-methyl-buten-1-al

Chromium trioxide (145 g., 1.45 mol) was added to 5 l. of methylene chloride in a 12 l. round bottomed flask fitted with an argon inlet and mechanical stirrer. Pyridine (230 ml., 2.9 mol) was added thereto and the resulting mixture was stirred for 2 hours. Celite (290 g.) and then E-4,4-dimethoxy-2-fluoro-3-methyl-buten-1-ol was added in one portion thereto and stirring continued for 30 minutes. The resulting mixture was filtered, evaporated at 30° C. to about 5% of its volume and diluted with 500 ml. of ether. The diluted mixture was filtered and evaporated to about 100 ml. at 30° C. to yield E-4,4-dimethoxy-2-fluoro-3-methyl-buten-1-al.

EXAMPLE 15

Methyl-2(E,Z),4(E),6(E)-8,8-dimethoxy-3,7-dimethyl-6-fluoro-octatrienoate

In a manner similar to that described in Example 12, E-4,4-dimethoxy-2-fluoro-3-methylbuten-1-al was treated at −60° C. with an anion prepared from 64 g. (0.29 mol) of dimethyl-(2-methyl-3-carbomethoxy-2-propen-1-yl) phosphonate and 126 ml. (0.29 mol) of 2.3 M n-butyllithium in 2000 ml. of anhydrous tetrahydrofuran. The reaction mixture was allowed to warm to room temperature for 2 days. The reaction mixture then was poured into 3 l. of water and extracted with 1.5 l. of hexane. The organic layer was washed twice with 1 l. of water and with 0.5 l. of a saturated sodium chloride solution, dried with 100 g. of sodium sulfate, filtered and evaporated. The resulting crude material (35 g.) was filtered through 150 g. of silica gel with 500 ml. of methylene chloride as elutant. Evaporation of the solvent gave 31.0 g. (41%) of methyl 2(E,Z),4(E),6(E)-8,8-dimethoxy-3,7-dimethyl-6-fluoro-octatrienoate.

EXAMPLE 16

Methyl 2(E,Z),4)E,6(E)-3-methyl-6-fluoro-7-formyl-2,4,6-octatrienoate

In a manner similar to that described in Example 12, 31 g. of methyl 2(E,Z),4(E),6(E)-8,8-dimethoxy-3,7-dimethyl-6-fluoro-octatrienoate were dissolved in 250 ml. of hexane and the resulting mixture was placed in an argon atmosphere. 250 ml. of 3 N aqueous hydrochloric acid were added thereto while vigorously stirring. A yellow solid formed. After 0.5 hours, the yellow solid was dissolved in 300 ml. of diethyl ether. The organic layer was separated and the aqueous phase was extracted with 100 ml. of hexane. The combined organic extracts were washed with 200 ml. of water and 200 ml. of a saturated aqueous sodium chloride solution, dried with 50 g. of anhydrous sodium sulfate, filtered and evaporated. Crystallization from 500 ml. of ether-hexane (1:2 parts by volume) at <20° C. gave 11.0 g. of 2(E,Z),4(E),6(E)-3-methyl-6-fluoro-7-formyl-2,4,6-octatrienoate. The mother liquor in 250 ml. of ether at −70° C. gave an additional 10.0 g. of the above ester (total yield 83%).

EXAMPLE 17

Methyl (2E,4E,6Z,8E)-3,7-dimethyl-6-fluoro-9-(2,4,5-trimethyl-3-thienyl)-nona-2,4,6,8-tetranoate (2,4,5-trimethyl-3-thenyl)-triphenylphosphonium chloride (11.9 g., 27.3 mmol) 5.3 g. of methyl 2(E),4(E),6(Z)-3-methyl-6-fluoro-7-formyl-2,4,6-octatrienoate and 500 ml. of butylene oxide were mixed under a stream of argon and refluxed for 2.5 hours until a clear solution developed. The solvent was evaporated therefrom. The residue was taken up in 400 ml. of hexane, washed twice with 150 ml. of 60% aqueous methanol then once with 200 ml. of a saturated sodium chloride solution, dried over 50 g. of sodium sulfate, filtered and evaporated.

Purification of the material by column chromatography on 300 g. of silica gel and elution with ether-hexane (3:7 parts by volume) gave methyl 2(E),4(E),6(Z),8(E)-3,7-dimethyl-6-fluoro-9-(2,4,5-trimethyl-3-thienyl)-nona-2,4,6,8-tetraenoate as the more polar product. After successive crystallizations from 50 ml. of ether-hexane (1:1 parts by volume) and 25 ml. of ether, 2.0 g. (24%) of pure methyl 2(E),4(E),6(Z),8(E)-3,7-dimethyl-6-fluoro-9-(2,4,5-trimethyl-3-thienyl)-nona-2,4,6,8-tetraenoate were obtained.

EXAMPLE 18

Methyl 2(E),4(E),6(Z),8(E)-3,7-dimethyl-6-fluoro-9-(2,3-dimethyl-4-methoxy-6-chlorophenyl)-nona-2,4,6,8-tetraenoate 2,3-dimethyl-4-methoxy-6-chlorobenzyl triphenylphosphonium chloride (4.2 g., 8.75 mmol), 1.6 g., (7.5 mmol) of methyl 2(E),4(E),6(Z)-3-methyl-6-fluoro-7-formyl-2,4,6-octatrienoate, 120 ml. of butylene oxide, and 80 ml. of toluene were combined and heated at 110° C. for 4 hours until a clear soluton resulted. The solvent was evaporated. The remaining crude material was dissolved in 500 ml. of hexane, washed twice with 300 ml. of 60% aqueous methanol, then once with 200 ml. of saturated sodium chloride solution, dried with 50 g. of sodium sulfate, filtered and evaproated.

Two crystallizations from isopropyl ether gave 1.45 g. (51%) of methyl 2(E),4(E),6(Z),8(E)-3,7-dimethyl-6-fluoro-9-(2,3-dimethyl-4-methoxy-6-chlorophenyl)-nona-2,4,6,8-tetraenoate.

EXAMPLE 19

Methyl 2(E),4(E),6(Z),8(E)-3,7-dimethyl-6-fluoro-9-(2,4,5-trimethyl-3-furyl)-nona-2,4,6,8-tetraenoate (2,4,5-trimethyl-3-furylmethyl) triphenylphosphonium bromide (5.1 g., 10.9 mmol) was suspended in 50 ml. of anhydrous tetrahydrofuran in a 100-ml. three-necked, round-bottomed flask fitted with an argon inlet, internal thermometer and septum. n-Butyllithium (2.3 M, 7.9 ml.) was added slowly thereto at −30° C. and the resulting mixture was stirred for 20 minutes until a clear solution resulted. Methyl 2(E),4(E),6(Z)-3-methyl-6-fluoro-7-formyl-2,4,6-octatrienoate (2.0 g, 9.4 mmol) in 5 ml. of tetrahydrofuran was added in one portion thereto and stirring continued at 0° C. for 0.5 hours. The resulting solution was poured into 300 ml. of hexane, washed with 100 ml. of 60% aqueous methanol then once with 100 ml. of a saturated sodium chloride solution, dried with 50 g. of sodium sulfate, filtered and evaporated. The resulting crude material was dissolved in methylene chloride and filtered through 60 g. of silica gel. Evaporation of the solvent gave 2.8 g. of an isomeric mixture. This mixture was dissolved in 100 ml. of dry benzene and treated with 20 mg. of iodine to induce isomerization. After 14 hours, the solution was washed with 50 ml. of 5% aqueous sodium thiosulfate, once with 50 ml. of water and once with 50 ml. of a saturated sodium chloride solution, dried with 50 g. of sodium sulfate, filtered and evaporated. Two crystallizations from isopropyl ether gave 1.5 g. (50%) of methyl 2(E),4(E),6(Z),8(E)-3,7-dimethyl-6-fluoro-9-(2,4,5-trimethyl-3-furyl)-nona-2,4,6,8-tetraenoate.

EXAMPLE 20

Methyl2(E),4(E),6Z),8(E)-3,7-dimethyl-6-fluoro-9-(2,6-dichloro-3-methyl-4-methoxyphenyl)-nona-2,4,6,8-tetraenoate (2,6-Dichloro-3-methyl-4-methoxybenzyl) triphenyl phosphonium chloride (3.86 g., 7.7 mmol) was suspended in 50 ml. of tetrahydrofuran in a 100-ml. three-necked, round-bottomed flask fitted with an argon inlet, internal thermometer and septum. n-Butyllithium (2.3 M, 3.6 ml.) was added slowly at −70° C. thereto and the temperature was allowed to rise to about 30° C. until a clear solution was obtained. Methyl 2(E),4(E),6(Z)-3-methyl-6-fluoro-7-formyl-2,4,6-octatrienoate in 5 ml. of tetrahydrofuran was added at −70° C. thereto. The resulting mixture was stirred at 0° C. for 0.5 hours, poured into water and extracted with 200 ml. of ether-ethyl acetate (1:1 parts by volume). The organic layer was washed with 200 ml. of a saturated sodium chloride solution, dried with 50 g. of sodium sulfate, filtered and evaporated. The resulting material was filtered through 80 g. of silica gel with methylene chloride as elutant. The solvent was evaporated and two crystallizations of the residue from 40 ml. of ethyl acetate-isopropyl ether (1:1 parts of volume) gave 1.32 g. (47%) of methyl 2(E),4(E),6(Z),8(E)-3,7-dimethyl-6-fluoro-9-(2,6-dichloro-3-methyl-4-methoxyphenyl)-nona-2,4,6,8-tetraenoate.

EXAMPLE 21

Methyl 2(E),4(E),6(Z),8(E)-3,7-dimethyl-6-fluoro-9-(2,4,6-trimethyl-3-chlorophenyl)-nona-2,4,6,8-tetraenoate (2,4,6-trimethyl-3-chlorobenzyl) triphenyl phosphonium chloride (7.5 g., 16.1 mmol) was suspended in 50 ml. of anhydrous tetrahydrofuran in a 100-ml. three-necked, round-bottomed flask fitted with an argon inlet, internal thermometer and septum, n-Butyllithium (2.3 M, 10 ml., 23 mmol) was added slowly at −30° C. and stirring continued until a clear solution resulted. Methyl 2(E),4(E),6(Z)-3-methyl-6-fluoro-7-formyl-2,4,6-octatrienoate (3.2 g., 15.1 mmol) was added at −30° C. The resulting mixture was allowed to come to 0° C. and stirring was continued for 0.5 hours. The resulting mixture was poured into water and extracted with 250 ml. of hexane. The organic phase was washed with water then with 100 ml. of a saturated sodium chloride solution, dried with 50 g. of sodium sulfate, filtered and evaporated. The resulting crude material was filtered through 100 g. of silica gel with methylene chloride as elutant. The solvent was evaporated. The residue was dissolved in 150 ml. benzene, treated with 10 mg. of iodine to bring about isomerization and allowed to stand for 5 days. The resulting solution was evaporated and the residue was purified by chromatography through 140 g. of silica gel and eluted with ether-hexane (1:4 parts by volume). Two crystallizations from 40 ml. isopropyl ether gave 1.28 g. (23%) of methyl 2(E),-4(E),6(Z),8(E)-3,7-dimethyl-6-fluoro-9-(2,4,6-trimethyl-3-chlorophenyl)-nona-2,4,6,8-tetraenoate.

EXAMPLE 22

Methyl 2(E),4(E),6(Z),8(E)-3,7-dimethyl-6-fluoro-9-(2,3,6-trichloro-4-methoxyphenyl)-nona-2,4,6,8-tetraenoate (2,3,6-trichloro-4-methoxybenzyl) triphenyl phosphonium chloride (4.5 g., 8.7 mmol), 1.8 g., (8.6 mmol) of methyl 2(E),4(E),6(Z)-3-methyl-6-fluoro-7-formyl-2,4,6-octatrienoate, 150 ml. of butylene oxide and 200 ml. of toluene were mixed and heated at 90°-100° C. for 5.5 hours until a clear solution resulted. The solvent was evaporated and the resulting crude material was passing through 200 g. of silica gel with methylene chloride as elutant. The solvent was evaporated and the residue was recrystallized from 2 l. of isopropyl ether and 500 ml. ethyl acetate to give 1.4 g. (40%) of methyl 2(E),-4(E),6(Z),8(E)-3,7-dimethyl-6-fluoro-9-(2,3,6-trichloro-4-methoxyphenyl)-nona-2,4,6,8-tetraenoate.

EXAMPLE 23

Methyl 2(E),4(E),6(Z),8(E)-3,7-dimethyl-6-fluoro-9-(2-chloro-3,6-dimethyl-4-methoxyphenyl)-nona-2,4,6,8-tetraenoate (2,Chloro-3,6-dimethyl-4-methoxybenzyl) triphenyl phosphonium chloride (4.1 g., 8.54 mmol), 1.8 g. (8.65 mmol) of methyl 2(E),4(E),6(Z)-3-methyl-6-fluoro-7-formylocta-2,4,6-trienoate, 75 ml. of toluene and 75 ml. of butylene oxide were mixed and heated to 80°-90° C. for 15 hours. The solvent was evaporated therefrom and the residue was filtered through 50 g. of silica gel with methylene chloride as elutant. The resulting product was crystallized once from isopropyl ether to give 1.25 g. (80%) of methyl2(E),4(E),6(Z),8(E)-3,7-dimethyl-6-fluoro-9-(2-chloro-3,6-dimethyl-4-methoxyphenyl)-nona-2,4,6,8-tetraenoate.

EXAMPLE 24

2E,4E,6Z,8E-3,7-dimethyl-6-fluoro-9-(2,4,5-trimethyl-3-thienyl)-2,4,6,8-nonatetraenoic acid A solution of 0.5 g. (12.5 mmol) of sodium hydroxide in 4 ml. of water was added to a solution of 1.0 g. (3 mmole) of methyl 2E,4E,6Z,8E-3,7-dimethyl-6-fluoro-9-(2,4,5-trimethyl-3-thienyl)-2,4,6,8-nonatetraenoate in 10 ml. of absolute ethanol. The mixture was stirred at 45° C. for 4 hours. The solution was cooled to room temperature, acidified with 3 N hydrochloric acid and filtered. The crude orange solid was purified by silica gel chromatography, euted with hexane-ethyl acetate (3:5 parts by volume) and crystallized from hexane-ethyl acetate (1:1 parts by volume) to give 600 mg. (62% yield) of 2E,4E,6Z,8E-3,7-dimethyl-6-fluoro-9-(2,4,5-trimethyl-3-thienyl)-2,4,6,8-nonatetraenoic acid orange crystals, m.p. 217°-223° C.

EXAMPLE 25

N-Ethyl (2E,4E,6Z,8E)-3,7-dimethyl-6-fluoro-9-(2,4,5-trimethyl-3-thienyl)-2,4,6,8-nonatetraenamide A suspension of 0.25 g. (0.78 mmole) of 2E,4E,6Z,8E-3,7-dimethyl-6-fluoro-9-(2,4,5-trimethyl-3-thienyl)-2,4,6,8-nonatetraenoic acid in 15 ml. of dry benzene was stirred at 23° C. under argon while about 5 mg. of dimethylformamide were added thereto followed by 0.20 g. (1.57 mmole) of oxalylchloride in 5 ml. of dry benzene. After one hour of stirring, dry ethylamine was bubbled into the resulting orange solution until a bright yellow color persisted. The reaction mixture was poured into water, extracted with ethyl acetate, washed with water, dried with magnesium sulfate, filtered and evaporated to give a crude orange solid. This material was purified by chromatography on silica gel using ethyl acetate-hexane (1:1 parts by volume) as elutant. One crystallization from ethyl acetate-hexane (1:1 parts by volume) gave 130 mg. (48% yield) of pure N-ethyl (2E,4E,6Z-,8E)-3,7-dimethyl-6-fluoro-9-(2,4,5-trimethyl-3-thienyl)-2,4,6,8-nonatetraenamide, m.p. 167°-171° C.

EXAMPLE 26

2E,4E,6Z,8E-3,7-dimethyl-6-fluoro-9-(2,4,5-trimethyl-3-thienyl)-2,4,6,8-nonatetraenamide A suspension of 0.40 g. (0.12 mmol) of 2E,4E,6Z,8E-3,7-dimethyl-6-fluoro-9-(2,4,5-trimethyl-3-thienyl)-2,4,6,8-nonatetraenoic acid in 12 ml. of dry benzene was stirred at 23° C. under argon while about 5 mg. of dimethylformamide were added thereto followed by 0.24 g. (0.19 mmole) of oxalyl chloride in 3 ml. of dry benzene. After 1 hour of stirring, dry ammonia was bubbled into the resulting orange solution until a bright yellow color persisted. The reaction mixture was poured into water, extracted with ethyl acetate, washed with water, dried with magnesium sulfate, filtered, and evaporated to give a crude orange solid. This material was purified by chromatography on silica gel using ethyl acetate-hexane (2:3 parts by volume) as the elutant. One crystallization from ethyl acetate gave 70 mg. (18% yield) of pure 2E,4E,6Z,8E-3,7-dimethyl-6-fluoro-9-(2,4,5-trimethyl-3-thienyl)-2,4,6,8-nonatetraenamide, m.p. 212°–215° C.

EXAMPLE 27

2E,4E,6Z,8E-dimethyl-6-fluoro-9-(2,4,5-trimethyl-3-thienyl)-2,4,6,8-nonatetraen-1-ol A solution of 1.05 g. (31.4 mmole) of methyl 2E,4E,6Z,8E-3,7-dimethyl-6-fluoro-9-(2,4,5-trimethyl-3-thienyl)-2,4,6,8-nonatetraenoate in 100 ml. of methylene chloride was cooled to $-60°$ C. under argon and 5.2 ml. (69 mmole) of diisobutylaluminium hydride were added dropwise thereto. The temperature was raised to $-10°$ C. for 10 minutes and 4 ml. of a saturated solution of magnesium sulfate were added thereto. This mixture was stirred at 25° C. for 2 hours, filtered through celite and evaporated to give a light yellow solid which was crystallized from hexane-ether (4:1 parts by volume) to give 700 mg. (73% yield) of 2E,4E,6Z,8E-3,7-dimethyl-6-fluoro-9-(2,4,5-trimethyl-3-thienyl)-2,4,6,8-nonatetraen-1-ol, m.p. 106°–107.5° C.

EXAMPLE 28

2E,4E,6Z,8E-3,7-dimethyl-6-fluoro-9-(2,4,5-trimethyl-3-thienyl)-2,4,6,8-nonatetraen-1-al A solution of 0.20 g. (0.65 mmole) of 2E,4E,6Z,8E-3,7-dimethyl-6-fluoro-9-(2,4,5-trimethyl-3-thienyl)-2,4,6,8-nonatetraen-1-ol in 20 ml. of methylene chloride was added to a suspension of 1.1 g. of activated manganese dioxide in 40 ml. of methylene chloride and stirred for 2 hours. The resulting mixture was filtered through celite and evaporated to give a bright orange solid which was crystallized from ether-hexane (1:4 parts by volume) to give 155 mg. (78% yield) of orange crystals of 2E,4E,6Z,8E-3,7-dimethyl-6-fluoro-9-(2,4,5-trimethyl-3-thienyl)-2,4,6,8-nonatetraen-1-al, m.p. 129°–131° C.

EXAMPLE 29

2E,4E,6Z,8E-3,7-dimethyl-6-fluoro-9-(2,4,5-trimethyl-3-thienyl)-1-methoxy-2,4,6,8-nonatetraene A solution of 0.400 g. (1.31 mmole) of 2E,4E,6Z,8E-3,7-dimethyl-6-fluoro-9-(2,4,5-trimethyl-3-thienyl)-2,4,6,8-nonatetraen-1-ol in 5 ml. of tetrahydrofuran was added to a suspension of 0.11 g. (2.6 mmole) of a 56% sodium hydride dispersion in a mixture of 10 ml. of dry tetrahydrofuran and 20 ml. of dry dimethylformamide. This reaction mixture was stirred at 23° C. for 14 hours, poured into water and extracted with ether-hexane (1:1 parts by volume). The extracts were washed with water, dried with magnesium sulfate, filtered and evaporated to give an orange product which was crystallized from ether-hexane (1:4 parts by volume) to give 220 mg. (52% yield) of 2E,4E,6Z,8E-3,7-dimethyl-6-fluoro-9-(2,4,5-trimethyl-3-thienyl)-1-methoxy-2,4,6,8-nonatetraene as a light orange solid, m.p. 117°–118° C.

EXAMPLE 30

2E,4E,6Z,8E-3,7-dimethyl-6-fluoro-9-(2,6-dichloro-3-methyl-4-methoxyphenyl)-2,4,6,8-nonatetraenoic acid In a manner similar to that described in Example 24, 1.2 g. (3 mmol) of methyl-(2E,4E,6Z,8E)-3,7-dimethyl-6-fluoro-9-(2,6-dichloro-3-methyl-4-methoxyphenyl)-nonatetraenoate were dissolved in 10 ml. of methanol and treated with a solution of 0.59 g. of sodium hydroxide in 4 ml. of water. The work-up as described in Example 24 afforded 2E,4E,6Z,8E-3,7-dimethyl-6-fluoro-9-(2,6-dichloro-3-methyl-4-methoxyphenyl)-2,4,6,8-nonatetraenoic acid.

EXAMPLE 31

(2E,4E,6Z,8E)-3,7-dimethyl-6-fluoro-9-(2,6-dichloro-3-methyl-4-methoxyphenyl)-2,4,6,8-nonatetraenamide A suspension of 385 mg. (1 mmole) of 2E,4E,6Z,8E-3,7-dimethyl-6-fluoro-9-(2,6-dichloro-3-methyl-4-methoxyphenyl)-nonatetraenoic acid was suspended in 15 ml. of dry benzene and treated as described in Example 26. Work-up as described therein and purification by silica gel chromatography afforded (2E,4E,6Z,8E)-3,7-dimethyl-6-fluoro-9-(2,6-dichloro-3-methyl-4-methoxyphenyl)-2,4,6,8-nonatetraenamide.

EXAMPLE 32

N-Ethyl(2E,4E,6Z,8E)-3,7-dimethyl-6-fluoro-9-(2,6-dichloro-3-methyl-4-methoxyphenyl)-2,4,6,8-nonatetraenamide In a manner similar to that described in Example 26, 385 mg. (1 mmole) of (2E,4E,6Z,8E)-3,7-dimethyl-6-fluoro-9-(2,6-dichloro-3-methyl-4-methoxyphenyl)-nonatetraenoic acid were suspended in 15 ml. of dry benzene and treated with oxalyl chloride and dimethylformamide, followed by dry ethylamine. Work-up as described in Example 26 afforded N-ethyl (2E,4E,6Z,8E)-3,7-diemthyl-6-fluoro-9-(2,6-dichloro-3-methyl-4-methoxyphenyl)-2,4,6,8-nonatetraenamide.

EXAMPLE 33

(2E,4E,6Z,8E)-3,7-dimethyl-6-fluoro-9-(2,6-dichloro-3-methyl-4-methoxyphenyl)-2,4,6,8-nonatetraen-1-ol Methyl(2E,4E,6Z,8E)-3,7-dimethyl-6-fluoro-9-(2,6-dichloro-3-methyl-4-methoxyphenyl)-2,4,6,8-nonatetraenoate (1.2 g., 3 mmol) was dissolved in methylene chloride and treated with diisobutylaluminum hydride in a hexane solution as described above in Example 27. Work-up as described therein afforded 2E,4E,6Z,8E-3,7-dimethyl-6-fluoro-9-(2,6-dichloro-3-methyl-4-methoxyphenyl)-2,4,6,8-nonatetraen-1-ol.

EXAMPLE 34

2E,4E,6Z,8E-3,7-dimethyl-6-fluoro-9-(2,6-dichloro-3-methyl-4-methoxyphenyl)-2,4,6,8-nonatetraen-1-al In a manner similar to that described in Example 28, 500 mg. (1.3 mmol) of 2E,4E,6Z,8E-3,7-dimethyl-6-fluoro-9-(2,6-dichloro-3-methyl-4-methoxyphenyl)-2,4,6,8-nonatetraen-1-ol were dissolved in 10 ml. of methylene chloride and added to a suspension of 2.5 g. of manganese dioxide in 50 ml. of methylene chloride. Work-up as described in Example 28 afforded 2E,-4E,6Z,8E-3,7-dimethyl-6-fluoro-9-(2,6-dichloro-3-methyl-4-methoxyphenyl)-2,4,6,8-nonatetraen-1-al.

EXAMPLE 35

(2E,4E,6Z,8E)-3,7-dimethyl-6-fluoro-9-(2,6-dichloro-3-methyl-4-methoxyphenyl)-1-methoxy-2,4,6,8-nonatetraene In a manner similar to that described in Example 29, a solution of 500 mg. (1.3 mmol) of (2E,4E,6Z,8E)-3,7-dimethyl-6-fluoro-9-(2,6-dichloro-3-methyl-4-methoxyphenyl)-2,4,6,8-nonatetraen-1-ol in 5 ml. of tetrahydrofuran was added to a suspension of sodium hydride in tetrahydrofuran and dimethylformamide. Work-up as described in Example 29 afforded (2E,4E,6Z,8E)-3,7-dimethyl-6-fluoro-9-(2,6-dichloro-3-methyl-4-methoxyphenyl)-1-methoxy-2,4,6,8-nonatetraene.

EXAMPLE 36

Ethyl 2Z,4E-2-fluoro-3-methyl-5-(2,6-dichloro-3-methyl-4-methoxyphenyl)-pentadienoate A suspension of 13 g. (26 mmol) of (2,6-dichloro-3-methyl-4-methoxyphenyl)-triphenylphosphonium chloride in tetrahydrofuran was stirred under argon and cooled to −70° C. The ylide was formed by the addition of 1.1 equivalent of n-butyllithium. The mixture was warmed to −35° C. for 15 minutes and a solution of 4.0 g. (25 mmol) of ethyl 2Z-2-fluoro-3-formyl-2-butenoate in 25 ml. of ethyl ether was added slowly. The mixture was warmed to 0° C., poured into water and extracted with ether. The ether extracts were washed with water and saturated sodium chloride solution, dried, and evaporated. The crude material was purified by partitioning between hexane and 60% methanol/water solution. The hexane phase was washed with water and a saturated sodium chloride solution, dried and evaporated. Silica gel chromatography afforded 4.9 g. (57% yield) of ethyl 2Z,4E-2-fluoro-3-methyl-5-(2,6-dichloro-3-methyl-4-methoxyphenyl)-pentadienoate.

EXAMPLE 37

2Z,4E-2-fluoro-3-methyl-5-(2,6-dichloro-3-methyl-4-methoxyphenyl)-pentadien-1-ol A solution of 8.5 g. (24.5 mmol) of ethyl 2Z,4E-2-fluoro-3-methyl-5-(2,6-dichloro-3-methyl-4-methoxyphenyl)pentadienoate was stirred under argon and cooled to −45° C. Diisobutylaluminum hydride (DIBAH) was added slowly until three equivalents had been added and no starting material remained by tlc. Saturated aqueous sodium sulfate (5 ml.) was added at −10° C. and the mixture was allowed to warm to 30° C. for completion of hydrolysis. The mixture was filtered through Celite and the filtrate was evaporated. The residue was chromatographed on silica to give 6.0 g. (80% yield) of 2Z,4E-2-fluoro-3-methyl-5-(2,6-dichloro-3-methyl-4-methoxyphenyl)pentadien-1-ol.

EXAMPLE 38

2Z,4E-2-fluoro-3-methyl-5-(2,6-dichloro-3-methyl-4-methoxyphenyl)-pentadien-1-al A solution of 5.6 g. (18.4 mmol) of 2Z,4E-2-fluoro-3-methyl-5-(2,6-dichloro-3-methyl-4-methoxyphenyl)-pentadien-1-ol in ether was added to a stirred suspension of 24 g. of activated manganese dioxide in ether. After 14 hours, thin layer chromatography indicated that all of the alcohol had reacted. The mixture was filtered through Celite. The filtrate was concentrated and the residue was chromatographed on silica gel to give 5.4 g. (95% yield) of 2Z,4E-2-fluoro-3-methyl-5-(2,6-dichloro-3-methyl-4-methoxyphenyl)pentadien-1-al.

EXAMPLE 39

Methyl(2E,4E,6Z,8E)-3,7-dimethyl-6-fluoro-9-(2,6-dichloro-3-methyl-4-methoxyphenyl)-2,4,6,8-nonatetraenoate A solution of 4.4 g. (20 mmol) of methyl(E,Z)-3-methyl-4-(dimethoxyphosphinyl)-2-butenoate, stirred under argon in tetrahydrofuran, was cooled to −60° C. and the ylide was formed by the addition of 1.1 equivalents of n-butyllithium. 5.0 G. (16.5 mmol) of 2Z,4E-2-fluoro-3-methyl-5-(2,6,-dichloro-3-methyl-4-methoxyphenyl)pentadien-1-al was dissolved in 40 ml. of tetahydrofuran and added at −30° C. After warming to 0° C., the reaction was poured into water and extracted with ether. The ether extracts were washed with water, dried and evaporated. After purification by silica gel chromatography, 2.2 g. (22% overall yield from ester) of methyl (2E,4E,6Z,8E)-3,7-dimethyl-6-fluoro-9-(2,6-dichloro-3-methyl-4-methoxyphenyl)nonatetraenoate, m.p. 179°–181° C. and 3.4 g. of a mixture of isomers were obtained.

EXAMPLE 40

Ethyl(2E,4E)-2-fluoro-3-methyl-5-(2,4,5-trimethyl-3-thienyl)-2,4-pentadienoate

A suspension of 21.0 g. (48 mmol) of (2,4,5-trimethyl-3-thenyl)-triphenylphosphonium chloride in tetrahydrofuran was stirred under argon while being cooled to −60° C. The ylide was formed by adding 1.1 equivalents of n-butyllithium and warming to −35° C. for 15 minutes. A solution of 7.7 g. (48 mmol) of ethyl 2E-2-fluoro-3-formyl-2-butenoate in 50 ml. of anhydrous ether was added slowly. This mixture was warmed to 0° C., poured into water, extracted with hexane, washed twice with 60% methanol/water, water, saturated sodium chloride solution, dried and evaporated. Purification by silica gel chromatography gave 8.8 g. (58% yield) of ethyl (2E,4E)-2-fluoro-3-methyl-5-(2,4,5-trimethyl-3-thienyl)-2,4-pentadienoate.

EXAMPLE 41

2E,4E-2-fluoro-3-methyl-5-(2,4,5-trimethyl-3-thienyl)-2,4-pentadien-1-ol

A solution of 6.5 g. (23 mmol) of ethyl (2E,4E)-2-fluoro-3-methyl-5-(2,4,5-trimethyl-3-thienyl)-2,4-pentadienoate in diethyl ether was stirred under argon and cooled to −45° C. Diisobutylaluminum hydride (DIBAH) was added slowly until three equivalents had been added and no starting ester remained. Five ml. of a saturated solution of sodium sulfate was added to −10° C. and the mixture was allowed to come to 30° C. Filtration through Celite and subsequent washing of the residue with methylene chloride gave a clear yellow solution of 2E,4E-2-fluoro-3-methyl-5-(2,4,5-trimethyl-3-thienyl)-2,4-pentadien-1-ol which was carried on to the next step without further purification.

EXAMPLE 42

2E,4E-2-fluoro-3-methyl-5-(2,4,5-trimethyl-3-thienyl)-2,4-pentadien-1-al

The solution of 2E,4E-2-fluoro-3-methyl-5-(2,4,5-trimethyl-3-thienyl)-2,4-pentadien-1-ol in ether and methylene chloride was added to a rapidly stirred suspension of 40 g. of activated manganese dioxide in methylene chloride. After 14 hours of stirring at 25° C., thin layer chromatography indicated that no starting alcohol remained. The manganese dioxide was removed by filtration through Celite. The filtrate containing 2E,4E-2-fluoro-3-methyl-5-(2,4,5-trimethyl-3-thienyl)-2,4-pentadien-1-al was concentrated and used in the next step without further purification.

EXAMPLE 43

Methyl 3,7-dimethyl-6-fluoro-9-(2,4,5-trimethyl-3-thienyl)nona-2,4,6,8-tetraenoate A solution of 8.9 g. (40 mmol) of methyl (E,Z)-3-methyl-4-(dimethoxyphosphinyl)-2-butenoate in tetrahydrofuran was cooled to −60° C. The ylide was formed by the addition of 1.1 equivalents of n-butyllithium. A solution of 2E,4E-2-fluoro-3-methyl-5-(2,4,5-trimethyl-3-thienyl)-2,4-pentadien-1-al in methylene chloride-ether was added at −30° C. After warming to 0° C., the reaction mixture was poured into water, extracted with hexane, washed with water and saturated sodium chloride solution, dried and evaporated. The product, methyl 3,7-dimethyl-6-fluoro-9-(2,4,5-trimethyl-3-thienyl)nona-2,4,6,8-tetraenoate, a mixture of isomers, was carried on to the next step without further purification.

EXAMPLE 44

Methyl 2E,4E,6Z,8E-3,7-dimethyl-6-fluoro-9-(2,4,5-trimethyl-3-thienyl)-2,4,6,8-nonatetraenoate The isomeric mixture of methyl 3,7-dimethyl-6-fluoro-9-(2,4,5-trimethyl-3-thienyl)nona-2,4,6,8-tetraenoate was dissolved in 200 ml. of chloroform with stirring in a quartz reaction vessel. 50 Mg. of iodine was added and the solution was irradiated by a sunlamp. After 1 hour, the solution was washed with 5% aqueous sodium thiosulfate solution, saturated sodium chloride solution, dried, and evaporated. Purification by preparative high pressure liquid chromatography gave 2.65 g. of methyl 2E,4E,6Z,8E-3,7-dimethyl-6-fluoro-9-(2,4,5-trimethyl-3-thienyl)-2,4,6,8-nonatetraenoate, m.p. 126°–128° C. (17% yield overall).

EXAMPLE 45

Ethyl 2Z,4E-2-fluoro-3-methyl-5-(2,4,5-trimethyl-3-furyl)-pentadienoate

A suspension of 35 g. (75 mmol) of 2,4,5-trimethyl-3-furyl-triphenylphosphonium bromide in tetrahydrofuran was stirred under argon and cooled to −60° C. The ylide was formed by adding 1.1 equivalents of n-butyllithium and warming to −35° C. for 15 minutes. A solution of 10.6 g. (66 mmol) of ethyl 2Z-2-fluoro-3-formyl-butenoate in 50 ml. of ether was added slowly. After warming to 0° C., the reaction was poured into water and extracted with hexane. This was purified by partitioning between hexane and a 60% methanol/water solution. The hexane phase was washed with water, dried and partially evaporated. This solution containing ethyl 2Z,4E-2-fluoro-3-methyl-5-(2,4,5-trimethyl-3-furyl)pentadienoate was carried on to the next step without further purification.

EXAMPLE 46

2Z,4E-2-fluoro-3-methyl-5-(2,4,5-trimethyl-3-furyl)-pentadien-1-ol

A solution of crude ethyl 2Z,4E-2-fluoro-3-methyl-5-(2,4,5-trimethyl-3-furyl)pentadienoate in ether was stirred under argon and cooled to −45° C. Diisobutylaluminum hydride (DIBAH) (112 mmol) was added slowly until no starting material remained. Five ml. of a saturated solution of sodium sulfate was added at −10° C. and the mixture was allowed to warm to 30° C. for a completion of hydrolysis. Filtration through Celite and evaporation gave 12 g. of 2Z,4E-2-fluoro-3-methyl-5-(2,4,5-trimethyl-3-furyl)pentadien-1-ol which was carried on to the next step without further purification.

EXAMPLE 47

2Z,4E-2-fluoro-3-methyl-5-(2,4,5-trimethyl-3-furyl)-pentadien-1-al

A solution of crude 2Z,4E-2-fluoro-3-methyl-5-(2,4,5-trimethyl-3-furyl)pentadien-1-ol in ether was added to a stirred suspension of 80 g. of activated manganese dioxide in ether. After 14 hours, all of the starting alcohol had reacted. The mixture was filtered through Celite and the filtrate was evaporated to give 5.5 g. of 2Z,4E-2-fluoro-3-methyl-5-(2,4,5-trimethyl-3-furyl)pentadien-1-al as an unstable orange oil. This was carried on to the next step without further purification.

EXAMPLE 48

Methyl(2E,4E,6Z,8E)-3,7-dimethyl-6-fluoro-9-(2,4,5-trimethyl-3-furyl)-2,4,6,8-nonatetraenoate A solution of 12.0 g. (54 mmol) of methyl (E,Z)-3-methyl-4-(dimethoxyphosphinyl)-2-butenoate in tetrahydrofuran was stirred under argon and cooled to −60° C. The ylide was formed by the addition of 1.1 equivalents of n-butyllithium. 5.5 G. of crude 2Z,4E-2-fluoro-3-methyl-5-(2,4,5-trimethyl-3-furyl)pentadien-1-al in 20 ml. of tetrahydrofuran was added at −30° C. After warming to 0° C., the reaction was poured into water and extracted with hexane. The organic phase was washed with a saturated sodium chloride solution and water, dried and evaporated. After purification by silica gel chromatography, 1.1 g. (5% overall yield from the pentadienote) of methyl (2E,4E,6Z,8E)-3,7-dimethyl-6-fluoro-9-(2,3,5-trimethyl-3-furyl)-2,4,6,8-nonatetraenoate, m.p. 122°–126° C. and 3.0 g. of a mixture of isomers were obtained.

EXAMPLE 49

Wet Granulation Tablet Formulation:

|  | mg/tablet | | |
| --- | --- | --- | --- |
|  | 10 | 20 | 40 |
| 1. Ethyl(E,Z,E,E)-9-(3-chloro-2,4,6-trimethyl-phenyl)-4-fluoro-3,7-dimethyl-2,4,6,8-nonatetraenoate | 10.0 | 20.0 | 40.0 |
| 2. Lactose | 264.0 | 255.0 | 273.0 |
| 3. Pregelatinized Starch | 17.5 | 17.5 | 20.0 |

-continued

|  | mg/tablet | | |
|---|---|---|---|
|  | 10 | 20 | 40 |
| 4. Cornstarch | 35.0 | 35.0 | 40.0 |
| 5. Modified Starch | 17.5 | 17.5 | 20.0 |
| 6. Magnesium Stearate | 6.0 | 6.0 | 7.0 |
| Total | 350 mg. | 350 mg. | 400 mg. |

Procedure:
1. Mix Items 1-5 in a suitable mixer, granulate with water. Dry overnight in an oven. Mill through a Fitzpatrick mill.
2. Mix with Item 6 and compress on a suitable press.

EXAMPLE 50

Wet Granulation Tablet Formulation:

|  | mg/tablet | | |
|---|---|---|---|
|  | 10 | 20 | 40 |
| 1. Methyl (2E,4E,6Z,8E)-3,7-dimethyl-6-fluoro-9-(2,4,5-trimethyl-3-thienyl)-nona-2,4,6,8-tetraenoate | 10.0 | 20.0 | 40.0 |
| 2. Lactose | 264.0 | 255.0 | 273.0 |
| 3. Pregelatinized Starch | 17.5 | 17.5 | 20.0 |
| 4. Cornstarch | 35.0 | 35.0 | 40.0 |
| 5. Modified Starch | 17.5 | 17.5 | 20.0 |
| 6. Magnesium Stearate | 6.0 | 6.0 | 7.0 |
| Total | 350 mg. | 350 mg. | 400 mg. |

Procedure:
1. Mix Items 1-5 in a suitable mixer, granulate with water. Dry overnight in an oven. Mill through a Fitzpatrick mill.
2. Mix with Item 6 and compress on a suitable press.

EXAMPLE 51

Wet Granulation Tablet Formulation:

|  | mg/tablet | | |
|---|---|---|---|
|  | 10 | 20 | 40 |
| 1. Methyl 2(E),4(E),6(Z),8(E)-3,7-dimethyl-6-fluoro-9-(2,3-dimethyl-4-methoxy-chlorophenyl)-nona-2,4,6,8-tetraenoate | 10.0 | 20.0 | 40.0 |
| 2. Lactose | 264.0 | 255.0 | 273.0 |
| 3. Pregelatinized Starch | 17.5 | 17.5 | 20.0 |
| 4. Cornstarch | 35.0 | 35.0 | 40.0 |
| 5. Modified Starch | 17.5 | 17.5 | 20.0 |
| 6. Magnesium Stearate | 6.0 | 6.0 | 7.0 |
| Total | 350 mg. | 350 mg. | 400 mg. |

Procedure:
1. Mix Items 1-5 in a suitable mixer, granulate with water. Dry overnight in an oven. Mill through a Fitzpatrick mill.
2. Mix with Item 6 and compress on a suitable press.

EXAMPLE 52

Capsule Formulation:

|  | mg/capsule | | |
|---|---|---|---|
|  | 10 | 20 | 40 |
| 1. Ethyl(E,Z,E,E)-9-(3-chloro-2,4,6-trimethylphenyl)-4-fluoro-3,7-dimethyl-2,4,6,8-nonatetraenoate | 20.0 | 20.0 | 40.0 |
| 2. Lactose | 215.0 | 205.0 | 260.0 |
| 3. Cornstarch | 60.0 | 60.0 | 80.0 |
| 4. Magnesium Stearate | 3.0 | 3.0 | 4.0 |
| 5. Talc | 12.0 | 12.0 | 16.0 |
| Total | 300 mg. | 300 mg. | 400 mg. |

Procedure:
1. Mix Items 1-3 in a suitable mixer. Mill through suitable mill.
2. Mix with Items 4 and 5 and fill on capsule machine.

EXAMPLE 53

Capsule Formulation:

|  | mg/capsule | | |
|---|---|---|---|
|  | 10 | 20 | 40 |
| 1. Methyl (2E,4E,6Z,8E)-3,7-dimethyl-6-fluoro-9-(2,4,5-trimethyl-3-thienyl)-nona-2,4,6,8-tetraenoate | 10.0 | 20.0 | 40.0 |
| 2. Lactose | 215.0 | 205.0 | 260.0 |
| 3. Cornstarch | 60.0 | 60.0 | 80.0 |
| 4. Magnesium Stearate | 3.0 | 3.0 | 4.0 |
| 5. Talc | 12.0 | 12.0 | 16.0 |
| Total | 300 mg. | 300 mg. | 400 mg. |

Procedure:
1. Mix Items 1-3 in a suitable mixer. Mill through suitable mill.
2. Mix with Items 4 and 5 and fill on capsule machine.

EXAMPLE 54

Capsule Formulation:

|  | mg/capsule | | |
|---|---|---|---|
|  | 10 | 20 | 40 |
| 1. Methyl 2(E),4(E),6(Z),8(E)-3,7-dimethyl-6-fluoro-9-(2,3-dimethyl-4-methoxy-6-chlorophenyl)-nona-2,4,6,8-tetraenoate | 10.0 | 20.0 | 40.0 |
| 2. Lactose | 215.0 | 205.0 | 260.0 |
| 3. Cornstarch | 60.0 | 60.0 | 80.0 |
| 4. Magnesium Stearate | 3.0 | 3.0 | 4.0 |
| 5. Talc | 12.0 | 12.0 | 16.0 |
| Total | 300 mg. | 300 mg. | 400 mg. |

Procedure:
1. Mix Items 1-3 in a suitable mixer. Mill through suitable mill.
2. Mix with Items 4 and 5 and fill on capsule machine.

EXAMPLE 55

Direct Compression Tablet Formulation:

|  | mg/tablet | | |
|---|---|---|---|
|  | 10 | 20 | 40 |
| 1. Ethyl(E,Z,E,E)-9-(3-chloro-2,4,6- | | | |

-continued

|  | mg/tablet | | |
|---|---|---|---|
|  | 10 | 20 | 40 |
| trimethylphenyl)-4-fluoro-3,7-dimethyl-2,4,6,8-nonatetraenoate | 10.0 | 20.0 | 40.0 |
| 2. Lactose | 182.0 | 172.0 | 216.0 |
| 3. Microcrystalline Cellulose | 60.0 | 60.0 | 80.0 |
| 4. Modified Starch | 15.0 | 15.0 | 20.0 |
| 5. Cornstarch | 30.0 | 30.0 | 40.0 |
| 6. Magnesium Stearate | 3.0 | 3.0 | 4.0 |
| Total | 300 mg. | 300 mg. | 400 mg. |

Procedure:
1. Mix Items 1-5 in a suitable mixer for 1 to 15 minutes.
2. Add Item 6 and mix for 5 minutes. Compress on a suitable press.

EXAMPLE 56

Direct Compression Tablet Formulation:

|  | mg/tablet | | |
|---|---|---|---|
|  | 10 | 20 | 40 |
| 1. Methyl (2E,4E,6Z,8E)-3,7-dimethyl-6-fluoro-9-(2,4,5-trimethyl-3-thienyl)-nona-2,4,6,8-tetraenoate | 10.0 | 20.0 | 40.0 |
| 2. Lactose | 182.0 | 172.0 | 216.0 |
| 3. Microcrystalline Cellulose | 60.0 | 60.0 | 80.0 |
| 4. Modified Starch | 15.0 | 15.0 | 20.0 |
| 5. Cornstarch | 30.0 | 30.0 | 40.0 |
| 6. Magnesium Stearate | 3.0 | 3.0 | 4.0 |
| Total | 300 mg. | 300 mg. | 400 mg. |

Procedure:
1. Mix Items 1-5 in a suitable mixer for 1 to 15 minutes.
2. Add Item 6 and mix for 5 minutes. Compress on a suitable press.

EXAMPLE 57

Direct Compression Tablet Formulation:

|  | mg/tablet | | |
|---|---|---|---|
|  | 10 | 20 | 40 |
| 1. Methyl 2(E),4(E),6(Z),8(E)-3,7-dimethyl-6-fluoro-9-(2,3-dimethyl-4-methoxy-6-chlorophenyl)-nona-2,4,6,8-tetraenoate | 10.0 | 20.0 | 40.0 |
| 2. Lactose | 182.0 | 172.0 | 216.0 |
| 3. Microcrystalline Cellulose | 60.0 | 60.0 | 80.0 |
| 4. Modified Starch | 15.0 | 15.0 | 20.0 |
| 5. Cornstarch | 30.0 | 30.0 | 40.0 |
| 6. Magnesium Stearate | 3.0 | 3.0 | 4.0 |
| Total | 300 mg. | 300 mg. | 400 mg. |

Procedure:
1. Mix Items 1-5 In a suitable mixer for 1 to 15 minutes.
2. Add Item 6 and mix for 5 minutes. Compress on a suitable press.

EXAMPLE 58

Cream Formulation:

| Item | Ingredients | % w/w |
|---|---|---|
| 1 | Ethyl (E,Z,E,E)-9-(3-chloro-2,46-trimethylphenyl)-4-fluoro-3,7-dimethyl-2,4,6,8-nonatetraenoate | 0.01 |
| 2 | Stearic Acid | 17.50 |
| 3 | Isopropyl Palmitate | 5.00 |
| 4 | Beeswax | 4.00 |
| 5 | Glyceryl Monostearate | 7.00 |
| 6 | Butylated Hydroxytoluene | 0.10 |
| 7 | Propylparaben | 0.05 |
| 8 | Methylparaben | 0.20 |
| 9 | Disodium Edetate | 0.01 |
| 10 | Propylene Glycol | 12.00 |
| 11 | Distilled Water q.s. | 100.00 |

Procedure:
1. In a suitable jacketed container with stirrer, heat to 80° C. and dissolve Items 2-7. Add and dissolve Item 1. Maintain at 80° C.
2. In a separate container, heat to 80° C. Items 11, 12. Add and dissolve Items 8, 9.

EXAMPLE 59

Cream Formulation:

| Item | Ingredients | % w/w |
|---|---|---|
| 1 | Methyl(2E,4E,6Z,8E)-3,7-dimethyl-6-fluoro-9-(2,4,5-trimethyl-3-thienyl)-nona-2,4,6,8-tetraenoate | 0.01 |
| 2 | Stearic Acid | 17.50 |
| 3 | Isopropyl Palmitate | 5.00 |
| 4 | Beeswax | 4.00 |
| 5 | Glyceryl Monostearate | 7.00 |
| 6 | Butylated Hydroxytoluene | 0.10 |
| 7 | Propylparaben | 0.05 |
| 8 | Methylparaben | 0.20 |
| 9 | Disodium Edetate | 0.01 |
| 10 | Propylene Glycol | 12.00 |
| 11 | Distilled Water q.s. | 100.00 |

Procedure:
1. In a suitable jacketed container with stirrer, heat to 80° C. and dissolve Items 2-7. Add and dissolve Item 1. Maintain at 80° C.
2. In a separate container, heat to 80° C. Items 11, 12. Add and dissolve Items 8, 9.

EXAMPLE 60

Cream Formulation:

| Item | Ingredients | % w/w |
|---|---|---|
| 1 | Methyl 2(E),4(E),6(Z),8(E)-3,7-dimethyl-6-fluoro-9-(2,3-dimethyl-4-methoxy-6-chlorophenyl)-nona-2,4,6,8-tetraenoate | 0.01 |
| 2 | Stearic Acid | 17.50 |
| 3 | Isopropyl Palmitate | 5.00 |
| 4 | Beeswax | 4.00 |
| 5 | Glyceryl Monostearate | 7.00 |
| 6 | Butylated Hydroxytoluene | 0.10 |
| 7 | Propylparaben | 0.05 |
| 8 | Methylparaben | 0.20 |
| 9 | Disodium Edetate | 0.01 |
| 10 | Propylene Glycol | 12.00 |
| 11 | Distilled Water q.s. | 100.00 |

Procedure:
1. In a suitable jacketed container with stirrer, heat to 80° C. and dissolve Items 2-7. Add and dissolve Item 1. Maintain at 80° C.

2. In a separate container, heat to 80° C. Items 11, 12. Add and dissolve Items 8, 9.

EXAMPLE 61

Ointment Formulation:

| Item | Ingredients | % w/w |
|---|---|---|
| 1 | Ethyl(E,Z,E,E)-9-(3-chloro-2,46-trimethylphenyl)-4-fluoro-dimethyl-2,4,6,8-nonatetraenoate | 0.01 |
| 2 | Mineral Oil | 10.00 |
| 3 | Hydrogenated Lanolin | 20.00 |
| 4 | Microcrystalline Wax | 2.50 |
| 5 | Butylated Hydroxytoluene | 0.10 |
| 6 | Petrolatum q.s. | 100.00 |

Procedure:
1. In a suitable container with stirrer, melt Items 2-6.
2. Add and dissolve Item 1 in Step 1.
3. Cool while stirring to room temperature.

EXAMPLE 62

Ointment Formulation:

| Item | Ingredients | % w/w |
|---|---|---|
| 1 | Methyl (2E,4E,6Z,8E)-3,7-dimethyl-6-fluoro-9-2,4,5-trimethyl-3-thienyl)-nona-2,4,6,8-tetraenoate | 0.01 |
| 2 | Mineral Oil | 10.00 |
| 3 | Hydrogenated Lanolin | 20.00 |
| 4 | Microcrystalline Wax | 2.50 |
| 5 | Butylated Hydroxytoluene | 0.10 |
| 6 | Petrolatum q.s. | 100.00 |

Procedure:
1. In a suitable container with stirrer, melt Items 2-6.
2. Add and dissolve Item 1 in Step 1.
3. Cool while stirring to room temperature.

EXAMPLE 63

Ointment Formulation:

| Item | Ingredients | % w/w |
|---|---|---|
| 1 | Methyl 2(E),4(E),6(Z),8(E)-3,7-dimethyl-6-fluoro-9-(2,3-dimethyl-4-methoxy-6-chlorophenyl)-nona-2,4,6,8-tetraenoate | 0.01 |
| 2 | Mineral Oil | 10.00 |
| 3 | Hydrogenated Lanolin | 20.00 |
| 4 | Microcrystalline | 2.50 |
| 5 | Butylated Hydroxytoluene | 0.10 |
| 6 | Petrolatum q.s. | 100.00 |

Procedure:
1. In a suitable container with stirrer, melt Items 2-6.
2. Add and dissolve Item 1 in Step 1.
3. Cool while stirring to room temperature.

We claim:
1. A compound having the formula:

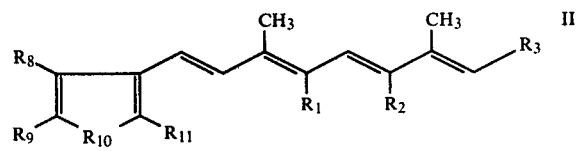

wherein one of $R_1$ and $R_2$ is fluorine and the other is hydrogen; $R_3$ is formyl, hydroxymethyl, alkoxymethyl, carboxyl, alkoxycarbonyl, carbamoyl, mono(lower alkyl)-carbamoyl or di(lower alkyl)-carbamoyl; $R_8$ and $R_{11}$ each are lower alkyl; $R_9$ is hydrogen or lower alkyl; and $R_{10}$ is oxygen; or pharmaceutically acceptable salts thereof.

2. The compound of claim 1 wherein the compound is all trans.

3. The compound of claim 1 or 2 wherein $R_3$ is alkoxycarbonyl or carboxyl.

4. The compound of claim 1 or 2 wherein $R_3$ is carbamoyl, mono(lower alkyl)-carbamoyl or di(lower alkyl)-carbamoyl.

5. The compound of claim 1 wherein the compound is methyl 2(E),4(E),6(Z),8(E)-3,7-dimethyl-6-fluoro-9-(2,4,5-trimethyl-3-furyl)-nona-2,4,6,8-tetraenoate.

* * * * *